United States Patent [19]
Deich et al.

[11] Patent Number: 5,108,744
[45] Date of Patent: Apr. 28, 1992

[54] VACCINES FOR HAEMOPHILUS INFLUENZAE

[75] Inventors: Robert A. Deich, Rochester; Gary W. Zlotnick, Penfield; Bruce A. Green, Pittsford, all of N.Y.

[73] Assignee: Praxis Biologics, Inc., Rochester, N.Y.

[21] Appl. No.: 434,625

[22] Filed: Nov. 9, 1989

Related U.S. Application Data

[63] Continuation of Ser. No. 948,364, Dec. 31, 1986, abandoned.

[51] Int. Cl.$^5$ .............................................. A61K 39/02
[52] U.S. Cl. ......................................... 424/92; 514/2; 530/350; 530/403
[58] Field of Search ........................... 424/88, 92, 87; 530/806, 808, 820-825, 350, 405

[56] References Cited

U.S. PATENT DOCUMENTS 4,591,552  5/1986  Neurath .............................. 436/534

OTHER PUBLICATIONS

Burans, J. et al., Infect & Immun., 41 No. 1:285-293 (1983).
Munson, R. et al., Infect & Immun. 49 No. 3:544-549 (1985).
Murphy, T. et al., Infect & Immun. 54 No. 3:774-779 (1986).
Anderson et al., 1972, J. Clin. Invest. 51:31-38.
Barenkamp et al., 1982, Infect. Immun. 36:535-40.
Barnekamp et al., 1981, J. Infect. Dis. 143:668-76.
Coulton et al., 1983, Can. J. Microbiol. 29:280-87.
Gnehm et al., 1985, J. Clin. Invest. 75:1645-58.
Granoff et al., 1986, J. Infect. Dis. 153:448-61.
Gulig et al., 1982, Infect. Immun. 37:82-88.
Hansen et al., 1982, Lancet, Feb. 12, 1982, pp. 366-68.
Hansen et al., 1981, Infect. Immun. 32:1084-92.
Lam et al., 1980, Current Microbiol. 3:359-64.
Loeb et al., 1982, Infect. Immun. 37:1032-36.
Loeb et al., 1981, J. Bacteriol. 145:596-05.
Loeb et al., 1980, Infect. Immun. 30:709-17.
Munson et al., 1984, Abstracts of the ICAAC: 234; No. 829.
Murphy et al., 1985, J. Infect. Dis. 152:1300-07.
Murphy et al., 1984, Abstracts of the ICAAC 234; No. 831.
Murphy et al., 1983, J. Infect. Dis. 147:838-46.
Shenep et al., 1983, Infect. Immun. 42:257-63.
Solotorovsky et al., 1978, in CRC Critical Reviews in Microbiology pp. 1-32.
van Alphen et al., 1983, FEMS Microbiol. Lett. 18:189-95.
van Alphen et al., 1983, J. Bacteriol. 155:878-85.
Wallace et al., 1981, J. Infect. Dis. 144:101-06.
Wright et al., International Publ. No. WO86/02360.

*Primary Examiner*—Sam Rosen
*Attorney, Agent, or Firm*—Alan M. Gordon; Geraldine F. Baldwin

[57] ABSTRACT

Peptides and proteins related to an epitope comprising an outer membrane protein of *Haemophilus influenzae* are described. The peptides and proteins can be prepared by methods includng novel and improved methods of purification from *H. influenzae* cultures, and by recombinant DNA and chemical synthetic techniques. Additionally, recombinant vectors containing nucleotide sequence encoding PBOMP-1 and PBOMP-2 related peptides and proteins are also described. Recombinant vectors include plasmid DNA and viral DNA such as human viruses, animal viruses, insect viruses and bacteriophages that direct the expression of the PBOMP-1 and PBOMP-2 related peptides and proteins in appropriate host cells. The peptides, proteins and viruses both "live" and "inactivated" are used as immunogens in vaccine formulations to protect against *H. influenzae* infections. The peptides and proteins are also used as reagents in immunoassays as well as to prepare immunoglobulins for passive immunization. Use of the nucleotide sequences encoding the PBOMP related peptides and proteins in hybridization assays is also described.

14 Claims, 16 Drawing Sheets

E = EcoRI; B = BamHI; P = PstI; Bg = BglII; X = XmnI;

FIG. 10

```
         10         20         30         40         50         60
AGATCTCACA ACGGGCGTTT CAGAGGTACT TAGTACATCT TTTCTAGGCG AAAGTCCAAG 70         80         90        100        110        120
CCTCTCTCCA AATGGAATTA TGATTATTTA TAGTTCTACA CAGGGCTTAG GAAAGGTGCT 130        140        150        160        170        180
ACAATTGGTT TCTGCAGATG GTCGCTTTAA GGCGAGCCTT CCAGGAAGTG ATGGTCAAGT 190        200        210        220        230        240
TAAATTTCCA GCTTGGTCTC CATACTTAAC TAAATAAAAA ACTCATTTAG GAGAAATCTA 250        260        270        280        290        300
ATGAACAAAT TTGTTAAATC ATTATTAGTT GCAGGTCTG TAGCTGCATT AGCAGCTTGT 310        320        330        340        350        360
AGTTCATCTA ACAACGATGC TGCAGGCAAT GGTGCTGCTC AAACTTTTGG CGGTTACTCT 370        380        390        400        410        420
GTTGCTGATC TTCAACAACG TTACAATACC GTTTATTTCG GTTTTGATAA ATATGACATT 430        440        450        460        470        480
ACTGGTGAAT ACGTTCAAAT CTTAGATGCG CACGCTGCAT ATTTAAATGC AACACCAGCT 490        500        510        520        530        540
GCTAAAGTAT TAGTAGAAGG TAACACTGAT GAACGTGGTA CACCAGAATA CAACATCGCA 550        560        570        580        590        600
TTAGGCCAAC GTCGTGCAGA TGCAGTTAAA GGTTATTTAG CTGGTAAAGG TGTTGATGCT 610        620        630        640        650        660
GGTAAATTAG GCACAGTATC TTACGGTGAA GAAAAACCTG CAGTATTAGG TCATGATGAA 670        680        690        700        710        720
GCTGCATATT CTAAAAACCG TCGTGCAGTG TTAGCGTACT AATTCTTAAT ATTTCTAATA

730
CTTGAAAAAC AGGATCC
```

FIG. 11

```
ATG AAC AAA TTT GTT AAA TCA TTA TTA GTT GCA GGT TCT GTA GCT GCA TTA GCA GCT TGT
Met Asn Lys Phe Val Lys Ser Leu Leu Val Ala Gly Ser Val Ala Ala Leu Ala Ala Cys

AGT TCA TCT AAC AAC GAT GCT GCA GGC AAT GGT GCT CCA ACT TTT GGC GGT TAC TCT
Ser Ser Ser Asn Asn Asp Ala Ala Gly Asn Gly Ala Pro Thr Phe Gly Gly Tyr Ser

GTT GCT GAT CTT CAA CAA CGT TAC AAT ACC GTT TAT TTC GGT TTT GAT AAA TAT GAC ATT
Val Ala Asp Leu Gln Gln Arg Tyr Asn Thr Val Try Phe Gly Phe Asp Lys Tyr Asp Ile

ACT GGT GAA TAC GTT CAA ATC TTA GAT GCG CAC GCT GCA TAT TTA AAT GCA ACA CCA GCT
Thr Gly Glu Tyr Val Gln Ile Leu Asp Ala His Ala Ala Tyr Leu Asn Ala Thr Pro Ala

GCT AAA GTA TTA GTA GAA GTT AAC ACT GAT GAA CGT GGT ACA CCA GAA TAC AAC ATC GCA
Ala Lys Val Leu Val Glu Val Asn Thr Asp Glu Arg Gly Thr Pro Glu Tyr Asn Ile Ala

TTA GGC CAA CGT CGT GCA GAT GCA GAT GGT AAA GGT TAT TTA GCT GGT GTT GAT GCT
Leu Gly Gln Arg Arg Ala Asp Ala Asp Gly Lys Gly Tyr Leu Ala Gly Val Asp Ala

GGT AAA TTA GGC ACA GTA TCT TAC TAC GGT GAA GAA AAA CCT GCA GTA TTA GGT CAT GAT GAA
Gly Lys Leu Gly Thr Val Ser Tyr Tyr Gly Glu Glu Lys Pro Ala Val Leu Gly His Asp Glu

GCT GCA TAT TCT AAA AAC CGT CGT GCA GTG TTA GCG TAC TAA
Ala Ala Tyr Ser Lys Asn Arg Arg Ala Val Leu Ala Tyr End
```

FIG. 12

```
PBOMP-1:  tyr-asn-thr-val-tyr-phe-gly-asp-lys-tyr-asp-ile-thr-gly-[glu]-tyr-
T9:       tyr-asn-thr-val-tyr-phe-gly-asp-lys-tyr-asp-ile-thr-gly-[phe]-tyr- PBOMP-1:  val-[gln]-ile-leu-asp-ala-[his]-ala-ala-tyr-leu-asn-ala-thr-pro-ala-ala
T9:       val-[thr]-ile-----asp-ala-[asp]-ala-ala-tyr-leu-asn-ala-thr-pro-ala-ala
```

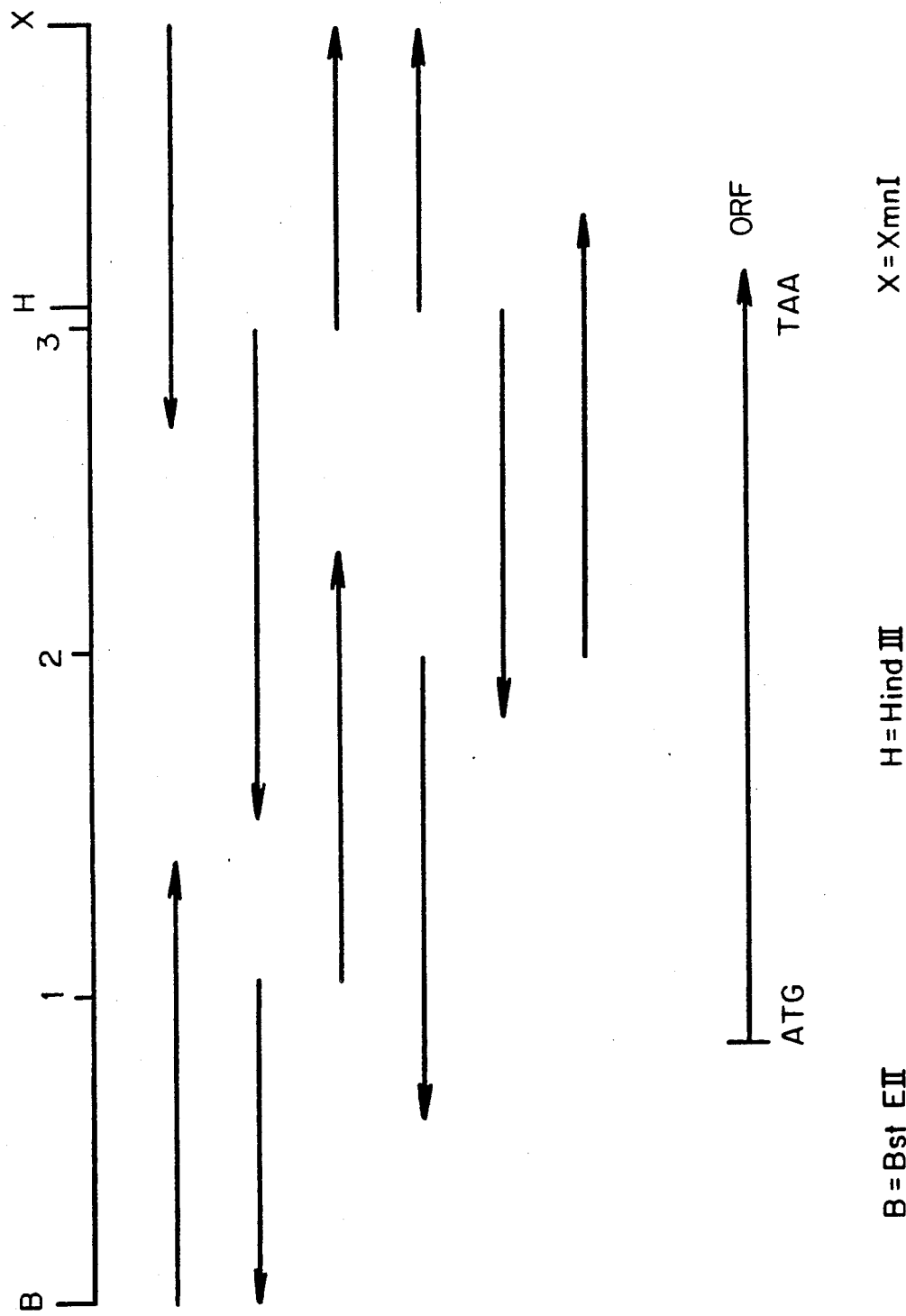

FIG. 14

```
          10         20         30         40         50         60
GGTAACCAGC AGAAAGGATA GGAGGTTGTT ATTGTGCATA AGTATGGTTC AACTTTAGTT 70         80         90        100        110        120
GTTGGTGCTT GTGTTTAGT  ATCTGACAAT GGTAATACTA AAAACATTTC AACTTTTTCT 130        140        150        160        170        180
CCAAGAAACC CACTTTAATT CCTTCTAATA TAGAGAATAT TATATGAAAA AAACAAATAT 190        200        210        220        230        240
GGCATTAGCA CTGTTAGTTG CTTTTAGTGT AACTGGTTGT GCAAATACTG ATATTTTCAG 250        260        270        280        290        300
CGGTGATGTT TATAGCGCAT CTCAAGCAAA GGAAGCGCGT TCAATTACTT ATGGTACGAT 310        320        330        340        350        360
TGTTTCTGTA CGCCCTGTTA AAATTCAAGC TGATAATCAA GGTGTAGTTG GTACGCTTGG 370        380        390        400        410        420
TGGTGGAGCT TTAGGTGGTA TTGCTGGTAG TACAATTGGC GGTGGTCGTG GTCAAGCTAT 430        440        450        460        470        480
TGCAGCAGTA GTTGGTGCAA TTGGCGGTGC AATAGCTGGA AGTAAAATCG AAGAAAAAAT 490        500        510        520        530        540
GAGTCAAGTA AACGGTGCTG AACTTGTAAT TAAGAAAGAT GATGGTCAAG AGATCGTTGT 550        560        570        580        590        600
TGTTCAAAAG GCTGACAGCA GTTTTGTAGC TGGTCGCCGA GTTCGTATTG TTGGTGGCGG 610        620        630        640        650        660
CTCAAGCTTA AATGTTTCTG TGCTATAACC AATAGCATTA AAGTCTAATA TGATTAATCA 670        680        690        700        710        720
GTGTCTTAAC TTAGTAAGGC ACTGATTTTT TTATAATTAA ATTCATTTAA AATATATATT 730        740        750        760        770        780
ATCGTCTATC TAAGATAAAT TTAAAGGACT AAATTAGAAT TTAGTCCTTT AGAAAACTTG

GAATTNNTTC
‿‿‿‿‿‿‿‿‿‿
  XmnI
```

FIG. 15

```
ATG AAA AAA ACA AAT ATG GCA TTA GCA CTG TTA GTT GCT TTT AGT GTA ACT GGT TGT GCA
Met Lys Lys Thr Asn Met Ala Leu Ala Leu Leu Val Ala Phe Ser Val Thr Gly Cys Ala

AAT ACT GAT ATT TTC AGC GGT GAT GTT TAT AGC GCA TCT CAA GCA AAG GAA GCG CGT TCA
Asn Thr Asp Ile Phe Ser Gly Asp Val Tyr Ser Ala Ser Gln Ala Lys Glu Ala Arg Ser

ATT ACT TAT GGT ACG AGT GTT TCT GTA CGC CCT GTT AAA ATT CAA GCT GAT AAT CAA GGT
Ile Thr Tyr Gly Thr Ser Val Ser Val Arg Pro Val Lys Ile Gln Ala Asp Asn Gln Gly

GTA GTT GGT ACG CTT GGT GGT GGA GCT TTA GGT GGT ATT GCT GGT AGT ACA ATT GGC GGT
Val Val Gly Thr Leu Gly Gly Gly Ala Leu Gly Gly Ile Ala Gly Ser Thr Ile Gly Gly

GGT CGT CAA GCT ATT GCA ATA GCA GTT GGT GCA GTA GTT GGT GCA ATA GCT GGA AGT
Gly Arg Gln Ala Ile Ala Ile Ala Val Val Gly Ala Val Val Gly Ala Ile Ala Gly Ser

AAA ATC GAA GAA AAA ATG AGT CAA GTA AAC GGT GCT GAA CTT GTA ATT AAG AAA GAT GAT
Lys Ile Glu Glu Lys Met Ser Gln Val Asn Gly Ala Glu Leu Val Ile Lys Lys Asp Asp

GGT CAA GAG ATC GTT GTT GTT CAA AAG GCT GAC AGC AGT TTT GTA GCT GGT CGC CGA GTT
Gly Gln Glu Ile Val Val Val Gln Lys Ala Asp Ser Ser Phe Val Ala Gly Arg Arg Val

CGT ATT GTT GGT GGC GGC TCA AGC TTA AAT GTT TCT GTG CTA TAA
Arg Ile Val Gly Gly Gly Ser Ser Leu Asn Val Ser Val Leu End
```

VACCINES FOR HAEMOPHILUS INFLUENZAE

This is a continuation, of application Ser. No. 948,364 filed Dec. 31, 1986, now abandoned.

TABLE OF CONTENTS

1. Field of the Invention
2. Background of the Invention
   2.1. Recombinant DNA Technology and Gene Expression
      2.1.1. *E. coli* as A Host System for Expression
      2.1.2. Vaccinia Virus as an Expression Vector
      2.1.3. Baculovirus as an Expression Vector
   2.2. *Haemophilus influenzae* and Disease
   2.3. Vaccines Against *H. influenzae*
3. Summary of Invention
4. Brief Description of the Figures
5. Detailed Description of the Invention
   5.1. Isolation and Purification of PBOMP-b 1
      5.1.1. Isolation of PBOMP-1 Enriched Insoluble Cell Wall Material From *H. influenzae*
      5.1.2. Solubilization of PBOMP-1 From the PBOMP-1Enriched Insoluble Cell Wall Material
   5.2. Characterization of PBOMP-1 by Amino Acid Analysis and Sequencing of PBOMP Peptides
   5.3. Molecular Cloning of Genes or Gene Fragments Encoding PBOMP-1 and PBOMP-2
      5.3.1. Isolation of Genes Encoding PBOMP-1 and Related PBOMPs
      5.3.2. Insertion of PBOMP Genes Into Expression Vectors
      5.3.3. Identification and Purification of the Expressed Gene Products
   5.4. Nucleotide Sequencing of PBOMP Genes
   5.5. Determination of Immunopotency of PBOMPs
   5.6. Formulation of a Vaccine
      5.6.1. Subunit Vaccine Formulations
      5.6.2. Viral Vaccine Formulations
      5.6.3. Passive Immunity and Anti-Idiotypic Antibodies
   5.7. Diagnostic Assays
      5.7.1. Immunoassays
      5.7.2. Nucleic Acid Hybridization Assays
6. Examples: Isolation and Characterization of Natural and Recombinant DNA-Derived PBOMPs
   6.1. Isolation, Purification and Analysis of PBOMP-1
      6.1.1. Characterization of PBOMP-1 by Amino Acid Composition and Sequence
   6.2. Preparation of Anti-PBOMP-1 Antibodies
      6.2.1. Preparation of Polyclonal Anti-PBOMP-1 Antiserum
      6.2.2. Production of Anti-PBOMP-1 Monoclonal Antibodies
   6.3. Reactivity of Anti-PBOMP-1 Antibodies with *E. coli*
   6.4 General Procedures Used for Preparation of Recombinant Plasmids
      6.4.1. Conditions for Restriction Enzyme Digestions
      6.4.2. Gel Purification of DNA Fragments
      6.4.3. DNA Ligation
      6.4.4. Protein Immuno Blot Analysis (Western Blot)
      6.4.5. Gene Fusions
      6.4.6. DNA Filter Hybridization Analysis (Southern Blot)
   6.5. Cloning the PBOMP Genes of *H. Influenzae*
      6.5.1. Construction of Hi Plasmid Library
      6.5.2. Construction of Hib Lambda Gene Bank
   6.6. Isolation of PBOMP Genes
      6.6.1. Isolation of a PBOMP Gene Encoding a Protein Which Reacts with Monoclonal Antibodies Against PBOMP-1
      6.6.2. Isolation of a PBOMP Gene Encoding a Protein Which Reacts with Polyclonal Anti-PBOMP-1 Antisera
   6.7 Determination of the Sequence of PBOMP Genes
      6.7.1. Sequencing Strategy for the PBOMP Gene Expressed by pAA152
      6.7.2. Sequencing Strategy for the PBOMPB Gene Expressed by pAA130
7. Efficacy of PBOMP-1 Subunit Vaccines
   7.1. Bactericidal Activity of Anti-Sera Induced by PBOMP-1
   7.2. Infant Rat Protection from *H. Influenzae*
8. Deposit of Microorganisms

1. FIELD OF THE INVENTION

The present invention relates to compositions and method for the preparation of proteins and peptides associated with the outer membrane of *Haemophilus influenzae*. More particularly, the invention is directed to compositions and methods for preparation of proteins and peptides related to a class of outer membrane proteins of about 16000 daltons molecular weight of type b and non-typable *H. influenzae* including PBOMP-1 and PBOMP-2. The proteins and peptides are used as immunogens in vaccine formulations for active immunization and for the generation of antibodies for use in passive immunization and as reagents in diagnostic assays.

The proteins and peptides can be obtained by novel improved methods of purification from *H. influenzae* or produced using either recombinant DNA or chemical synthetic methods. Additionally, the invention relates to novel DNA sequences and vectors useful for directing expression of PBOMP-1 and PBOMP-2 related proteins and peptides. The nucleotide sequences are used as reagents in nucleic acid hybridization assays.

2. BACKGROUND OF THE INVENTION

2.1. Recombinant DNA Technology and Gene Expression

Recombinant DNA technology involves insertion of specific DNA sequences into a DNA vehicle (vector) to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. Several general methods have been developed which enable construction of recombinant DNA molecules. For example, Cohen and Boyer U.S. Pat. No. 4,237,224 describes production of such recombinant plasmids using processes of cleavage with restriction enzymes and joining with DNA ligase by known methods of ligation. These recombinant plasmids are then introduced by means of transformation and replicated in unicellular cultures including procaryotic organisms and eucaryotic cells grown in tissue culture. Because of the general applicability of the techniques described therein, U.S. Pat. No. 4,237,224 is hereby incorporated by reference into the present specification.

Another method for introducing recombinant DNA molecules into unicellular organisms is described by Collins and Hohn in U.S. Pat. No. 4,304,863 which is also incorporated herein by reference. This method utilizes a packaging/transduction system with bacteriophage vectors (cosmids).

Recombinant genes may also be introduced into viruses, such as vaccina virus. Recombinant viruses can be generated by transfection of plasmids into cells infected with virus.

Regardless of the method used for construction, the recombinant DNA molecule must be compatible with the host cell, i.e., capable of autonomous replication in the host cell or stably integrated into one of the host cell's chromosomes. The recombinant DNA molecule or virus (e.g., a vaccinia virus recombinant) should also have a marker function which allows the selection of the desired recombinant DNA molecule(s) or virus(es). In addition, if all of the proper replication, transcription and translation signals are correctly arranged on the recombinant DNA molecule, the foreign gene will be properly expressed in the transformed bacterial cells, as is the case with bacterial expression plasmids, or in permissive cell lines infected with a recombinant virus or a recombinant plasmid carrying a eucaryotic origin of replication.

Different genetic signals and processing events control many levels of gene expression; for instance, DNA transcription and messenger RNA (mRNA) translation. Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system and further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, 1979, Methods in Enzymology 68:473.

Many other factors complicate the expression of foreign genes in procaryotes even after the proper signals are inserted and appropriately positioned. One such factor is the presence of an active proteolytic system in *E. coli* and other bacteria. This protein-degrading system appears to selectively destroy "abnormal" or foreign proteins. A tremendous utility, therefore, would be afforded by the development of a means to protect eucaryotic proteins expressed in bacteria from proteolytic degradation. One strategy is to construct hybrid genes in which the foreign sequence is ligated in phase (i.e., in the correct reading frame) with a procaryotic gene. Expression of this hybrid gene results in a fusion protein product (a protein that is a hybrid of procaryotic and foreign amino acid sequences).

Successful expression of a cloned gene requires efficient transcription of DNA, translation of the mRNA and in some instances post-translational modification of the protein. Expression vectors have been used to express genes in a suitable host and to increase protein production. The cloned gene should be placed next to a strong promotor which is controllable so that transcription can be turned on when necessary. Cells can be grown to a high density and then the promotor can be induced to increase the number of transcripts. These, if efficiently translated will result in high yields of protein. This is an especially valuable system if the foreign protein is deleterious to the host cell.

2.1.1. *E. coli* as a Host System for Expression

Most plasmid cloning vectors commonly used in *E. coli* are derivatives of ColE1-type replicons (for additional information see Oka et al., 1979, Mol. Gen. Genet. 172:151–159). The ColEI plasmids are stably maintained in *E. coli* strains as monomeric molecules with a copy number of about 15–20 copies per chromosome. Various levels of expression of human and animal protein products of foreign genes inserted into these plasmids have been obtained. However, very high expression levels should be obtained in order for the system to become economically feasible to produce foreign protein products.

One way to obtain large amounts of a given gene product is to clone a gene on a plasmid which has a very high copy number within the bacterial cell. In theory, by increasing the number of copies of a particular gene, mRNA levels should also increase which should lead to increased production of the recombinant protein.

2.1.2. Vaccinia Virus as an Expression Vector

Vaccinia virus may be used as a cloning and expression vector. The virus contains a linear double-stranded DNA genome of approximately 187 kb pairs which replicates within the cytoplasm of infected cells. These viruses contain a complete transcriptional enzyme system (including capping, methylating and polyadenylating enzymes) within the virus core which are necessary for virus infectivity. Vaccinia virus transcriptional regulatory sequences (promotors) allow for initiation of transcription by vaccinia RNA polymerase but not by eucaryotic RNA polymerase.

Expression of foreign DNA in recombinant viruses requires the fusion of vaccinia promotors to protein coding sequences of the foreign gene. Plasmid vectors, also called insertion vectors have been constructed to insert the chimeric gene into vaccina virus. One type of insertion vector is composed of: (1) a vaccinia virus promotor including the transcriptional initiation site; (2) several unique restriction endonuclease cloning sites downstream from the transcriptional start site for insertion of foreign DNA fragments; (3) nonessential vaccinia virus DNA (such as the TK gene) flanking the promotor and cloning sites which direct insertion of the chimeric gene into the homologous nonessential region of the virus genome; and (4) a bacterial origin of replication and antibiotic resistance marker for replication and selection in *E. coli*. Examples of such vectors are described by MacKett (1984, J. Virol. 49: 857–864).

Recombinant viruses are produced by transfection of recombinant bacterial insertion plasmids containing the foreign gene into cells infected with vaccinia virus.

Homologous recombination takes place within the infected cells and results in the insertion of the foreign gene into the viral genome. Recombinant viruses can be screened for and subsequently isolated using immunological techniques, DNA plaque hybridization, or genetic selection. These vaccinia recombinants retain their essential functions and infectivity and can be constructed to accommodate approximately 35 kb of foreign DNA.

Expression of a foreign gene can be detected by enzymatic or immunological assays [e.g., immunoprecipitation, enzyme-linked immunosorbent assay (ELISA), radioimmunoassay, or immunoblotting]. Additionally, naturally occurring membrane glycoproteins produced from recombinant vaccinia infected cells are glycosylated and may be transported to the cell surface. High expression levels can be obtained by using strong promotors or cloning multiple copies of a single gene in appropriate vectors and suitable hosts.

2.1.3. Baculovirus as an Expression Vector

A baculovirus, such as *Autographica californica* nuclear polyhedrosis virus (AcNPV) may also be used as a cloning or expression vector. The infectious form of AcNPV is normally found in a viral occlusion. This structure is largely composed of polyhedrin peptide in which virus particles are embedded. Polyhedrin gene expression occurs very late in the infection cycle, after mature virus particles are formed. Therefore polyhedrin gene expression is a dispensible function, i.e., non-occluded virus particles produced in the absence of polyhedrin gene expression are fully active and are capable of infecting cells in culture. According to European Patent Application Serial No. 84105841.5 by Smith et al., a recombinant baculovirus expression vector is prepared by cleaving baculovirus DNA to produce a fragment comprising a polyhedrin gene or portion thereof, inserting this fragment into a cloning vehicle and thereafter inserting the gene to be expressed such that it is under control of the polyhedrin gene promotor. The recombinant transfer vector formed in this way is mixed with baculovirus helper DNA and used to transfect insect cells in culture to effect recombination and incorporation of the selected gene at the polyhedrin gene locus of the baculovirus genome. The resultant recombinant baculovirus is used to infect susceptible insects or cultured insect cells.

2.2. Haemophilus influenzae and Disease

*H. influenzae* are divided into two groups. Those strains which posses a known capsule are typed by the serological reaction of the capsule with reference antisera. Types a-f have been identified. Strains which fail to react with any of the reference antisera are known as non-typable.

*H. influenzae* type b (Hib) is the most frequent cause of neonatal meningitis and other invasive infections in the Unites States (Fraser et al., 1974, Am. J. Epidemiol. 100:29-34). The major incidence of childhood meningitis occurs between the ages of one and five years. Sixty percent of those meningitis cases due to Hib occur in children under the age of two (Fraser et al., supra).

It is now well established that non-typable *H. influenzae* (Hi) also cause diseases including pneumonia, bacteremia, meningitis, postpartum sepsis, and acute febrile tracheobronchitis in adults (Murphy et al., 1985, J. Infect. Diseases 152: 1300-1307). Non-typable Hi are a frequent etiologic agent of otitis media in children and young adults, causing about 20 to 40% of all otitis media cases. Children may experience multiple infections due to the same organism since infection confers no long lasting immunity. Current therapy for chronic or repeated occurrences of otitis media includes administration of antibiotics and insertion of tubes to drain the inner ear. Hi strains have also been implicated as a primary cause of sinusitis (Cherry J. D. and J. P. Dudley, 1981, in Textbook of Pediatric Infectious Diseases, Feigin and Cherry eds., pp 103-105). Additionally, non-typable Hi cause neonatal sepsis.

Antiserum produced against the capsular polysaccharide of type b *H. influenzae* (Hib) which comprises polyribosyl ribitol phosphate (PRP), has been shown to be bactericidal and protective against Hib (Smith et al., 1973, Pediatrics 52:637-644; Anderson, et al., 1972, J. Clin. Inv. 51:31-38). Anti-PRP antibody is ineffective against non-typable *H. influenzae* infections.

2.3. Vaccines against *H. influenzae*

The ideal candidate for a Haemophilus vaccine would have three properties: a) it would be immunogenic in infants of 2-6 months (b) it would elicit an antibody which would protect against infections caused by typable and non-typable *H. influenzae*, and (c) it would elicit antibody against a determinant found on the surface of all strains of *H. influenzae*.

The currently available vaccines which protect against Hib infections consist essentially of PRP, the type b capsular polysaccharide. Purified PRP polysaccharide is immunogenic in children above 18 months of age, but does not elicit a protective antibody response in those younger than 18 months. In general, polysaccharides have been shown to be poor immunogens in children less than about 18 months of age.

To address this problem, various laboratories have begun studies in which PRP is either chemically coupled to a protein carrier molecule (Anderson et al., 1985, Ped. Res. 18:252A) or mixed with protein molecules (Monji et al., 1986, Infect. Immun. 51:865-871) and administered to animals or humans. Conjugation of PRP to protein has been shown to elicit an anti-PRP antibody response in human infants as young as 6 months, while a mixture of PRP with some proteins has produced anti-PRP antibody in infant animals (Monji et al., supra).

Although the conjugate and admixture vaccine formulations address one difficulty of PRP vaccines, i.e., their inability to protect infants younger than 18 months, they fail to address another major problem of the PRP vaccine. Anti-PRP antibody is ineffective against non-typable *H. influenzae*, which by definition lack the PRP capsule. Hence there is a long recognized need for a vaccine that will elicit a protective immune response in children of about 18 months and younger against both typable, including type b and non-typable *H. influenzae*.

One object of the present invention is to provide a vaccine formulation that elicits a protective immune response against typable *H. influenzae* including type b and non-typable *H. influenzae* in children under 6 months as well as in older children and adults. The approach of the present invention is to vaccinate with a protein or fragment thereof which is exposed on the surface of Haemophilus. The best candidate is an outer membrane protein (OMP) of *H. influenzae*. Outer membrane proteins are usually surface exposed molecules. They are composed of protein which is normally immunogenic in infants, and they have been shown to be capable of eliciting protective antibody in other bacterial systems (Sugasawara et. al., 1983, Infect. Immun. 42:980-985).

In addition Hi and Hib strains have been shown to have similar OMP profiles (Loeb and Smith, 1980, Infect. Immun. 30:709-717). Antibody to an OMP of Haemophilus could be both bactericidal and opsonic much as anti-PRP has been shown to be bactericidal and opsonic for Hib (Anderson et al., 1972, J. Clin. Invest. 51:31-38; Cates et al., 1985, Infect. Immun. 48:183-189). An outer membrane protein has the additional advantage of being common to Hi and Hib and could protect against both types of bacteria.

3. SUMMARY OF INVENTION

The present invention is directed to peptides and proteins related to an outer membrane protein of about 16000 daltons molecular weight of *Haemophilus influenzae* identified by applicants and termed "Praxis Biologics Outer Membrane Protein-1" (PBOMP-1) and to an antigenically related outer membrane protein of about 16000 daltons molecular weight of *Haemophilus influenzae* also identified by applicants and termed "Praxis Biologics Outer Membrabe Protein-2" (PBOMP-2), as well as the molecularly cloned genes or gene fragments which encode these peptides or proteins. The invention is also directed to a substantially pure PBOMP-1 obtained from *H. influenzae* using novel and improved methods. The peptides or proteins of the present invention may be used as immunogens in vaccine formulations for *H. influenzae*, or as reagents in diagnostic immunoassays for *H. influenzae*.

The present invention is also directed to methods for the molecular cloning of genes or gene fragments encoding PBOMP-1 and PBOMP-2 related peptides. These molecularly cloned sequences can then be used in the further construction of other vectors by recombinant DNA techniques, including expression vectors for the encoded peptide products, or in obtaining the PBOMP-1 and PBOMP-2 genes for use in diagnostic assays for *H. influenzae* based on nucleic acid hybridization.

The peptides or proteins of the present invention may be purified from *H. influenzae*, or produced using recombinant DNA techniques in any vector-host system, or synthesized by chemical methods. Accordingly, the invention is also directed to the construction of novel DNA sequences and vectors including plasmid DNA, and viral DNA such as human viruses, animal viruses, insect viruses, or bacteriophages which can be used to direct the expression of PBOMP-1 and PBOMP-2 related peptides or proteins in appropriate host cells from which the peptides and proteins may be purified. Chemical methods for the synthesis of PBOMP-1 and PBOMP-2 related peptides and proteins are described.

The PBOMP-1 and PBOMP-2 related peptides and proteins can be used as immunogens in subunit vaccine formulations for use against all pathogenic *H. influenzae*, including both type b and non-typable *H. influenzae*. PBOMP-1 and PBOMP-2 related proteins or peptides for subunit vaccine preparations can be obtained by chemical synthesis, purification from *H. influenzae* or purification from recombinant expression vector systems. Alternatively, recombinant viruses which produce the PBOMP-1 or PBOMP-2 related peptides or proteins themselves or extracts of cells infected with such recombinant viruses can be used as immunogens in viral vaccine formulations. Since the PBOMP-1 or PBOMP-2 protein will be recognized as "foreign" in the host animal, a humoral and possibly a cell-mediated immune response will be induced, directed against PBOMP-1 or PBOMP-2. In a properly prepared vaccine formulation, this should protect the host against subsequent *H. influenzae* infections. Moreover, the present subunit vaccine formulations will be compatible with currently available PRP vaccines.

The PBOMP-1-related and/or PBOMP-2 related sequences of the present invention can be used in human medical assays. These include the use of the peptides and proteins of the present invention as reagents in immunoassays such as ELISA tests and radioimmunoassays which are useful as diagnostic tools for the detection of *H. influenzae* infection in blood samples, body fluid, tissues, etc. The PBOMP-1 encoding and/or PBOMP-2-encoding gene sequences can be used in DNA-DNA or DNA-RNA hybridization assays for similar diagnostic detection of *H. influenzae*. Additionally, these reagents will provide a valuable tool in elucidating the mechanism of pathogenesis of *H. influenzae*.

The present invention is directed further to anti-PBOMP-1 and/or anti-PBOMP-2 monoclonal antibodies which have uses in passive immunization regimes, and in diagnostic immunoassays.

4. BRIEF DESCRIPTION OF THE FIGURES

The present invention may be more fully understood by reference to the following detailed description and examples of specific embodiments as well as the appended figures in which:

FIG. 1 represents sodium dodecylsulfate polyacrylamide gel electrophoretic (SDS-PAGE) analysis of PBOMP-1. Samples and gels were prepared as described in Section 6.1. Lane A contains about 5 ug PBOMP-1. Lane B contains prestained low molecular weight (MW) standards: ovalbumin, alpha-chymotrypsinogen, beta-lactoglobulin, lysozyme, bovine trypsin inhibitor and insulin (A and B chains). Relative MWs [in kilodaltons (kd)] are shown at the side.

FIG. 2 (A and B) represents reactivity of whole cell lysates of *E. coli* and *H. influenzae* with polyclonal anti-PBOMP-1 antibody and a monoclonal anti-PBOMP-1 antibody (G1-1). In FIG. 2A, lysates were reacted with polyclonal anti-PBOMP-1 antibody. Lanes are as follows: (1) *E. coli* HB101; (2) E. coli JM83; (3) molecular weight standards; (4) purified PBOMP-1 obtained from cultured *H. influenzae* cells. In FIG. 2B, lysates were reacted with monoclonal anti-PBOMP-1 antibody. Lanes are as described in FIG. 2A.

FIG. 3 represents a restriction map of pGD103, a derivative of pLG339 (see Stoker et al., 1982, Gene 18:335-41).

FIG. 4 (A and B) represents maps of pAA152 which comprises a 4.2 Kb fragment of *H. influenzae* DNA cloned into pGD103. A gene encoding PBOMP-1 is localized to an 737 bp BglII-BamHI fragment. FIG. 2A is a circular restriction map of pAA152. FIG. 2B illustrates deletion analysis of the inserted fragment of pAA152. The remaining *H. influenzae* DNA in the deletion derivatives is denoted by black lines. PBOMP phenotype is noted at the right.

FIG. 5 represents reactivity of whole cell lysates of *E. coli* JM83 containing pAA152 with individual monoclonal antibodies which react with different epitopes of PBOMP-1. Lanes are as follows: (A) monoclonal antibody G1-1; (b) monoclonal antibody G94-3; (C) monoclonal antibody G18-3; (D) monoclonal antibody 25-2; and (E) monoclonal antibody G2-3.

FIG. 6 represents autoradiographic analysis of DS410 minicells containing recombinant plasmids pAA130 and pAA152. Molecular weight standards are noted at the left of the figure. Lanes represent: (A) DS410 (pAA130); (B) DS410 (pGD103); and (C) DS410 (pAA152). The location of kanamycin aminoglycosidase is noted at the right of the figure.

FIG. 7 (A and B) represents maps of pAA130 which comprises a 5.7 Kb fragment of *H. influenzae* DNA cloned into pGD103. FIG. 7A represents a circular restriction map of pAA130. FIG. 7B represents deletion analysis of the *H. influenzae* inserted fragment of pAA130. Solid black lines denote remaining *H. influenzae* DNA in the deletion derivatives. PBOMP phenotype is noted at the right. A gene encoding PBOMP-2 is localized to a 781 bp BstEII-XmnI fragment.

FIG. 10 represents the nucleotide sequence of the 737 bp fragment which contains the PBOMP-1 gene. The predicted open reading frame (ORF) is shown by the underlined sequence and the direction of transcription indicated by the arrowhead.

Figure 2A:
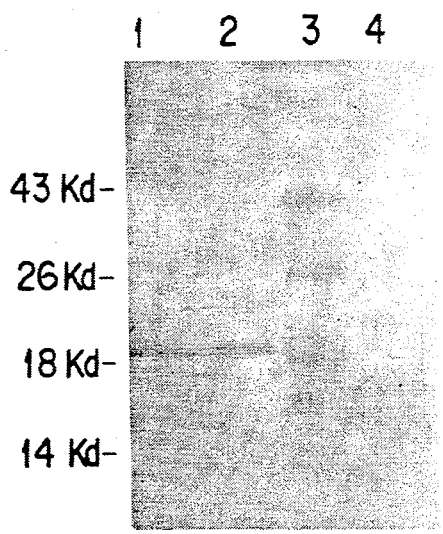

FIG. 11 represents the deduced amino acid sequence of PBOMP-1. The nucleotide sequence is depicted on the upper line and the corresponding amino acid sequence below. The amino acid enclosed within the box represents the predicted N-terminal amino acid of the mature form of the protein.

FIG. 12 represents alignment of the partial amino acid sequence of a peptide derived from PBOMP-1 (below) with a portion of the derived amino acid sequence of the PBOMP-1 gene (above). Residues enclosed within boxes represent mismatches.

FIG. 13 represents the sequencing strategy of the 789 bp BstEII-XmnI fragment of pAA130 showing the origin, direction and extent of sequence determined from each clone. The arrow at the bottom denotes the location of the major open reading frame (ORF).

FIG. 14 represents the nucleotide sequence of the 789 bp BstEII-XmnI fragment of pAA130 which contains the PBOMP-2 gene. The predicted ORF is shown by the underlined sequence. The direction of transcription is denoted by the arrowhead. The two bases designated "N" represent unknown nucleotides.

FIG. 15 represents the deduced amino acid sequence of PBOMP-2. The nucleotide sequence is depicted above and the corresponding amino acid sequence below. The residue enclosed within the box indicates the predicted N-terminal amino acid of the mature form of the protein.

5. DETAILED DESCRIPTION OF THE INVENTION

The present invention is directed to proteins and peptides related to epitopes of an approximately 16000 dalton molecular weight outer membrane protein of *H. influenzae*, i.e., PBOMP-1 and of a related approximately 16000 dalton molecular weight outer membrane protein of *H. influenzae*, i.e., PBOMP-2. The apparent molecular weights as determined using SDS-PAGE reflect the total molecular weights of the mature (i.e., proteolytically processed) forms, including any post-translational modification(s) (e.g., fatty acylation, acetylation, etc.). The proteins and peptides of the invention can be produced using recombinant DNA methods or by chemical synthesis. Additionally, the proteins and peptides of the invention can be obtained in substantially pure form from cultures of *H. influenzae* using novel and improved methods of isolation and purification. The PBOMP-1 and PBOMP-2 proteins and peptides specifying epitopes of *H. influenzae* can be used as immunogens in various vaccine formulations to protect against infection with *H. influenzae*, an etiological agent of bacterial meningitis, otitis media, epiglottitis, pneumonia, etc. The vaccine formulations are effective against both *H. influenzae* typable strains including types a, b, c, d, e, and f as well as non-typable *H. influenzae* strains.

The present invention further relates to the nucleotide sequence(s) of the genes encoding the PBOMP-1 and PBOMP-2 proteins as well as the amino acid sequences of the PBOMP-1 and PBOMP-2 proteins and polypeptide fragments thereof.

According to one embodiment of the present invention, recombinant DNA techniques are used to insert nucleotide sequences encoding PBOMP-1 and PBOMP-2 epitopes into expression vectors that will direct the expression of these sequences in appropriate host cells. These expression vector host cell systems can be used to produce PBOMP-1 and PBOMP-2 and related proteins and peptides. The gene products can be purified from cells in culture and used as immunogens in subunit vaccine formulations. Alternatively, the amino acid sequence of PBOMP-1 and PBOMP-2 proteins and peptides may be deduced either (1) from the substantially pure PBOMP-1 protein isolated from *H. influenzae* as taught herein or (2) from the *H. influenzae* nucleotide sequences contained in recombinants that express immunogenic PBOMP-1 or PBOMP-2 related proteins and peptides. These proteins and peptides may then be chemically synthesized and used in synthetic subunit vaccine formulations.

Where the expression vector that expresses the PBOMP-1 and/or PBOMP-2 sequences is a recombinant virus, the virus itself may be used as a vaccine. Infectious recombinant viruses that express the PBOMP-1 and/or PBOMP-2 proteins and peptides and that do not cause disease in a host can be used in live virus vaccine preparations to provide substantial immunity. Alternatively, inactivated virus vaccines can be prepared using "killed" recombinant viruses that express the PBOMP-1 and/or PBOMP-2 proteins and peptides.

The present invention is further directed to polyvalent antiserum and monoclonal antibody against PBOMP-1 and/or PBOMP-2 as well as methods for use of such immunoglobulin for passive immunization, and diagnostic assays for *H. influenzae*.

For the purpose of description, the method of the invention can be divided into the following stages: (1) isolation and purification of PBOMP-1 protein; (2) partial amino acid sequencing of PBOMP-1; (3) molecular cloning of genes or gene fragments encoding PBOMP-1 and PBOMP-2, including insertion of the genes or gene fragments into expression vectors and identification and purification of the recombinant gene products; (4) nucleotide sequencing of the genes encoding PBOMP-1 and PBOMP-2; and (5) determination of the immunopotency of the PBOMP-1 and PBOMP-2 proteins and related products through production of antibodies against purified and recombinant protein and peptide products. The method further encompasses (6) formulation of vaccines and (7) diagnostic assays for detection of PBOMP-1 and PBOMP-2 genes or gene product (and hence *H. influenzae*) in samples of body fluids.

5.1. Isolation and Purification of PBOMP-1

In *H. influenzae* b Eagan and other strains of *H. influenzae*, the outer membrane protein PBOMP-1 is associated with the outer membrane-cell wall complex. A necessary step in the purification of PBOMP-1 is the disruption of the bonds which keep the outer membrane proteins in tight association with the outer membrane and cell wall. This can be accomplished by the novel and improved method of the invention which comprises the following two stages: (1) isolating a PBOMP-1 enriched insoluble cell wall fraction from physically disrupted cells of *H. influenzae*, and then (2) solubilizing PBOMP-1 from the cell wall fraction by heating in the presence of a detergent which is suitable for administration to a human or digesting the cell wall fraction with lysozyme either in the presence or absence of detergent.

The novel improved method of the present invention avoids the use of denaturants and reducing agents such as sodium dodecylsulfate and 2-mercaptoethanol (see Munson et al., 1984, Infect. Immun. 49:544–49) which might destroy important epitopes and which are not suitable components for vaccine formulations for administration to humans.

5.1.1. Isolation of PBOMP-1 Enriched Insoluble Cell Wall Material from *H. influenzae*

A total cell membrane fraction may be obtained by differential sedimentation following disruption of *H. influenzae* cells by methods including but not limited to: sonication, grinding, by expulsion from a french press other homogenization device. The total membrane fraction may be further fractionated into inner and outer membranes by density gradient sedimentation or by differential solubilization of the inner membrane by certain detergents such as Triton X-100 ™ or N-lauroyl sarcosine, sodium salt (sarcosyl). Outer membranes are preferably prepared by differential solubilization of inner membranes in 1% (W/V) sarcosyl in 10 mM HEPES-NaOH, pH 7.4. A subfraction enriched in PBOMP-1 can be produced by differential detergent extraction of other outer membrane-cell wall components. This enrichment can be accomplished, for example, by sequential extraction of the outer membrane-cell wall complex (which remains after Tween-80 or sarcosyl extraction as described above) with 1% octylglucoside, nonylglucoside, zwittergent 3-14 ™, or zwittergent 3-16 ™, followed by extraction of the insoluble material with 1% sarcosyl, and then centrifugation to isolate the PBOMP-1 enriched insoluble material.

5.1.2. Solubilization of PBOMP-1 from the PBOMP-1 Enriched Insoluble Cell Wall Material Solubilization of the PBOMP-1 from the outer membrane-cell wall complex can be achieved in several different ways using one of the following approaches or a combination thereof: (1) PBOMP-1 can be solubilized by extraction of the PBOMP-1 enriched fraction with one or any combination of several detergents, including but not limited to deoxycholate, Triton X-100 ™, Tween 80, CHAPS, CHAPSO, dodecylmaltoside, zwittergent 3-14 ™, and zwittergent 3-16 ™, at 55° C.–60° C. for 1 hour; (2) PBOMP-1 can be solubilized by disruption of the cell wall in the PBOMP-1 enriched fraction with lysozyme, either in the presence or absence of detergent. According to a preferred embodiment the detergent is selected from: deoxycholate and polyethoxylate sorbitan monooleate (Tween-80).

Alternatively, PBOMP-1 can be isolated by extracting whole *H. influenzae* cells, outer membranes or subfractions thereof with one or a combination of detergents including but not limited to: Triton X-100 ™, sarcosyl, octylglucoside, nonylglucoside, zwittergent 3-14 ™, or zwittergent 3-16 ™. This extraction could be performed at 55°–60° C. or at room temperature in an appropriate buffer system.

After solubilization, further purification of the PBOMP-1 can be achieved by standard methods known in the art including but not limited to: ion exchange, molecular sieve, hydrophobic or reverse phase chromatography, affinity chromatography, chromatofocusing, isoelectric focusing and preparative electrophoresis.

5.2. Characterization of PBOMP-1 by Amino Acid Analysis and Sequencing of PBOMP Peptides The PBOMP-1 obtained from *H. influenzae* can be characterized by amino acid analysis in combination with partial amino acid sequencing of peptide fragments. In order to minimize the destruction and/or modification of amino acids in the purified protein it is preferable to hydrolyze the PBOMP-1 in methanesulfonic acid containing tryptamine (Simpson et al., 1970, J. Biol. Chem. 251:1936–40). In one experimental example of the present invention, such amino acid analysis was combined with amino acid sequencing of tryptic peptide fragments of PBOMP-1 to characterize the novel peptide isolated as described (see Section 6.1.1.).

5.3. Molecular Cloning of Genes or Gene Fragments Encoding PBOMP-1 and PBOMP-2

5.3.1. Isolation of Genes Encoding PBOMP-1 and Related PBOMPs

A 16000 dalton molecular weight (MW) OMP has been detected, both by sodium dodecyl sulfate polyacrylamide gel electrophoresis (SDS-PAGE) and Western Blot analysis in all *H. influenzae* strains tested (currently several hundred). Monoclonal antibody data indicate that this protein is highly conserved (Murphy et al., 1986, Infect. Immun. 54:774–49). Thus, any *H. influenzae* strain could serve as the source for the PBOMP genes. Since many *H. influenzae* strains contain no detectable plasmids or inducible prophages, the PBOMP genes are probably chromosomal. Accordingly, the first step in the molecular cloning of DNA sequences encoding PBOMPs is the isolation of such sequences from *H. influenzae* chromosomal DNA. Hereinafter, DNA encoding *H. influenzae* genes will be referred to as "Hi DNA", and DNA encoding PBOMPs sequences will be referred to as "PBOMP DNA".

In order to generate Hi DNA fragments, the Hi DNA may be cleaved at specific sites using various restriction enzymes. Alternatively, one may use low concentrations of DNAase I to fragment the DNA, or the DNA can be physically sheared, as for example, by sonication. The linear DNA fragments may then be separated according to size by standard techniques, including, but not limited to: agarose and polyacrylamide gel electrophoresis, column chromatography (e.g., molecular sieve or ion exchange chromatography) or velocity sedimentation in sucrose gradients.

Any restriction enzyme or combination of restriction enzymes may be used to generate the Hi DNA fragment(s) containing the PBOMP sequences provided the enzyme(s) does not destroy the immunopotency of the PBOMP gene products. For example, the antigenic site of a protein can consist of from about 7 to about 14 amino acids. Thus, a protein of the size of the PBOMP peptides may have many discrete antigenic sites and therefore, many partial PBOMP polypeptide gene sequences could code for an antigenic site. Consequently many restriction enzyme combinations may be used to generate DNA fragments, which, when inserted into an appropriate vector are capable of directing the production of PBOMP specific amino acid sequences comprising different antigenic determinants.

Once the DNA fragments are generated, identification of the specific DNA fragment containing the PBOMP gene may be accomplished in a number of ways.

The DNA sequences containing the PBOMP genes may be identified by hybridization of the Hi DNA fragments with a synthetic oligonucleotide probe. Redundant synthetic oligonucleotide probes are constructed based upon the amino acid sequence of peptide fragments of the PBOMP protein. For example, synthetic oligonucleotide probes can be prepared based upon the amino acid sequence of the substantially pure PBOMP-1 protein isolated from *H. influenzae* as described in Section 5.1. These synthetic probes can be radio-labeled with $^{32}$P-adenosine triphosphate and used to screen Hi DNA libraries for clones containing PBOMP-specific gene sequences (see Anderson et al., 1983, Proc. Nat'l Acad. Sci. USA 80: 6838–42).

Alternatively, the PBOMP gene DNA may be identified and isolated after insertion into a cloning vector in a "shotgun" approach. A large number of vector-host systems known in the art may be used. Vector systems may be either plasmids or modified viruses. Suitable cloning vectors include, but are not limited to the viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101 and other similar systems. The vector system must be compatible with the host cell used. Recombinant molecules can be introduced into cells via transformation, transfection or infection.

When Hi DNA containing a PBOMP gene or gene fragment is inserted into a cloning vector and used to transform appropriate host cells many copies of the PBOMP gene or gene fragment can be generated. This can be accomplished by ligating the Hi DNA fragment into a cloning vector which has complementary cohesive termini. If, however, the complementary restriction sites are not present, the ends of the DNA molecules may be modified. Such modification includes producing blunt ends by digesting back single-stranded DNA termini or by filling the single-stranded termini so that the ends can be blunt-end ligated. Alternatively, any site desired may be produced by ligating nucleotide sequences (linkers) onto the DNA termini. These ligated linkers may comprise specific chemically synthesized oligonucleotides encoding restriction site recognition sequences. For example, according to the DNA modification procedure of Maniatis, (see Maniatis et al., 1982, Molecular Cloning, Cold Spring Harbor Laboratory, pp. 107-114) sheared DNA is treated with a restriction methylase (for example, M. EcoRI) and ligated to synthetic DNA linkers which encode a restriction site for that enzyme. The DNA is then treated with restriction endonuclease to cleave the terminal linkers (but not the modified internal restriction sites) and ligated to the appropriate vector arms. In an alternative method, the cleaved vector and PBOMP DNA fragment may be modified by homopolymeric tailing.

Identification of a cloned PBOMP gene can be accomplished by establishing a chromosomal gene bank of Hi in a vector system and screening individual clones for the production of PBOMP-1 or PBOMP-1 related protein by any of the methods described herein, including, but not limited to specific reaction with polyclonal or monoclonal antibodies against PBOMPs.

5 3.2. Insertion of PBOMP Genes into Expression Vectors

The nucleotide sequences coding for PBOMPs or portions thereof, are inserted into an appropriate expression vector, i.e., a vector which contains the necessary elements for the transcription and translation of the inserted protein-coding sequences. A variety of host-vector systems may be utilized to express the protein-encoding sequence(s). Primarily the vector system must be compatible with the host cell used. Host-vector systems include but are not limited to the following: bacteria transformed with bacteriophage DNA, plasmid DNA or cosmid DNA; microorganisms such as yeast containing yeast vectors; mammalian cell systems infected with virus (=.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

In order to obtain efficient expression of the gene (or a portion of the gene), a promotor must be present in the expression vector. RNA polymerase normally binds to the promotor and initiates transcription of a gene or a group of linked genes and regulatory elements (called an operon). Promotors vary in their "strength", i.e., their ability to promote transcription. For the purpose of expressing a cloned gene, t is desirable to use strong promotors in order to obtain a high level of transcription and, hence, expression of the gene. Depending upon the host cell system utilized, any one of a number of suitable promotors may be used. For instance, when cloning in *E. coli*, its bacteriophages or plasmids, promotors such as the lac promotor, trp promotor, recA promotor, ribosomal RNA promotor, the $P_R$ and $P_L$ promotors of coliphage lambda and others including but not limited to lacUV5, ompF, bla, lpp and the like, may be used to direct high levels of transcription of adjacent DNA segments. Additionally, a hybrid trp-lacUV5 (tac) promotor or other E. coli promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the $P_L$ promotor of lambda can be induced by an increase in temperature in host cells containing a temperature sensitive lambda represor, e.g., cI857. In this way, greater than 95% of the promotor-directed transcription may be inhibited in uninduced cells. Thus, expression of the genetically engineered PBOMP protein or peptide thereof may be controlled. This is important if the protein product of the cloned gene is lethal or detrimental to host cells. In such cases, transformants may be cultured under conditions such that the promotor is not induced, and when the cells reach a suitable density in the growth medium, the promotor can be induced for production of the protein.

One such promotor/operator system is the so-called "tac" or trp-lac promotor/operator system (Russell and Bennett, 1982, Gene 20:231-243; DeBoer, European Patent Application, 67,540 filed May 18, 1982). This hybrid promotor is constructed by combining the −35 b.p. (−35 region) of the trp promotor and the −10 b.p. (−10 region or Pribnow box) of the lac promotor (the sequences of DNA which are the RNA polymerase binding site). In addition to maintaining the strong promotor characteristics of the tryptophan promotor, tac is also controlled by the lac repressor.

When cloning in a eucaryotic host cell, enhancer sequences (e.g., the 72 bp tandem repeat of SV40 DNA or the retroviral long terminal repeats or LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promotor elements (e.g., the polymerase binding site and the Goldberg-Hogness "TATA" box) which must be located immediately 5' to the gene, enhancer sequences have a remarkable ability to function upstream from, within, or downstream from eucaryotic genes; therefore, the position of the enhancer sequence with respect to the inserted gene is less critical.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in E. coli requires a Shine-Dalgarno (SD) sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the E. coli tryptophan E, D, C, B or A genes. Additionally, any SD-ATG combination produced by recombinant DNA or other techniques involving incorporation of synthetic nucleotides may be used.

Any of the methods previously described for the insertion of DNA fragments into a vector may be used to ligate a promotor and other control elements into specific sites within the vector.

Accordingly, H. influenzae genetic sequences containing those regions coding for the PBOMP proteins or peptides can be ligated into an expression vector at a specific site in relation to the vector promotor and control elements so that when the recombinant DNA molecule is introduced into a host cell the foreign genetic sequence can be expressed (i.e., transcribed and translated) by the host cell. The recombinant DNA molecule may be introduced into appropriate host cells (including but not limited to bacteria, virus, yeast, mammalian cells or the like) by transformation, transduction or transfection (depending upon the vector/host cell system). Transformants are selected based upon the expression of one or more appropriate gene markers normally present in the vector, such as ampicillin resistance or tetracycline resistance in pBR322, or thymidine kinase activity in eucaryotic host systems. Expression of such marker genes should indicate that the recombinant DNA molecule is intact and is replicating. Expression vectors may be derived from cloning vectors, which usually contain a marker function. Such cloning vectors may include, but are not limited to the following: SV40 and adenovirus, vaccinia virus vectors, insect viruses such as baculoviruses, yeast vectors, bacteriophage vectors such as lambda gt-WES-lambda B, Charon 28, Charon 4A, lambda gt-1-lambda BC, lambda gt-1-lambda B, M13mp7, M13mp8, M13mp9, or plasmid DNA vectors such as pBR322, pAC105, pVA51, pACYC177, pKH47, pACYC184, pUB110, pMB9, pBR325, Col E1, pSC101, pBR313, pML21, RSF2124, pCR1, RP4, pBR328 and the like.

Transfer of drug resistance factors between H. influenzae and E. coli via conjugation (Stuy, 1979, J. Bact. 139:520-529); and transformation (Mann, 1979, Plasmid 2:503-505) and cloning of Haemophilus chromosomal genes in E. coli (Mann et al., 1980, Gene 3:97-112) indicate that at least some genes can be efficiently expressed in both organisms; and that the basic mechanisms of transcriptional and translational control may be similar.

In the particular embodiment in the examples of the present invention, an E. coli plasmid system was chosen as the expression vector. The invention, however, is not limited to the use of such E. coli expression vector.

Genetic engineering techniques could also be used to further characterize and/or adapt the cloned gene. For example, site directed mutagenesis of the gene encoding a PBOMP protein could be used to identify regions of the protein responsible for generation of protective antibody responses. It could also be used to modify the protein in regions outside the protective domains, for example, to increase the solubility of the protein to allow easier purification.

5.3.3. Identification and Purification of the Expressed Gene Products

Expression vectors containing foreign gene inserts can be identified by three general approaches: (1) DNA-DNA hybridization using probes comprising sequences that are homologous to the foreign inserted gene; (2) presence or absence of "marker" gene functions (e.g., resistance to antibiotics, transformation phenotype, thymidine kinase activity, etc.); and (3) expression of inserted sequences based on the physical, immunological or functional properties of the gene product.

Once a recombinant which expresses a PBOMP gene is identified, the gene product should be analyzed. Immunological analysis is especially important because the ultimate goal is to use the gene products or recombinant viruses that express such products in vaccine formulations and/or as antigens in diagnostic immunoassays.

A variety of antisera are available for analyzing immunoreactivity of the product, including, but not limited to polyvalent antisera and monoclonal antibodies described in Section 6.2., infra.

Identification of the proteins and peptides of the invention requires that the PBOMP related protein or peptide be immunoreactive to a variety of antibodies directed against PBOMP or its analogs and derivatives.

The protein or peptide should be immunoreactive whether it results from the expression an entire PBOMP gene sequence, a portion of the gene sequence or from two or more gene sequences which are ligated to direct the production of fusion proteins. This reactivity may be demonstrated by standard immunological techniques, such as radio-immunoprecipitation, radioimmune competition, ELISA or immunoblots.

Once the *H. influenzae* PBOMP related protein is identified, it may be isolated and purified by standard methods including chromatography (e.g., ion exchange, affinity, and sizing column chromatography), centrifugation, differential solubility, or by any other standard techniques for the purification of proteins.

Alternatively, once an immunoreactive *H. influenzae* PBOMP related protein produced by a recombinant is identified, the amino acid sequence of the immunoreactive protein can be deduced from the nucleotide sequence of the chimeric gene contained in the recombinant. As a result, the protein can be synthesized by standard chemical methods known in the art (e.g., see Hunkapiller et al., 1984, Nature 310: 105-111).

In a particular embodiment of the present invention such peptides, whether produced by recombinant DNA techniques or by chemical synthetic methods, include but are not limited to all or part of the amino acid sequences substantially as depicted in FIG. 11 and/or FIG. 15 including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the non-polar (hydrophobic) amino acids include glycine, alanine, leucine, isoleucine, valine, proline, phenylalanine, tryptophan and methionine. The polar neutral amino acids include serine, threonine, cysteine, tyrosine, asparagine, and glutamine. The positively charged (basic) amino acids include arginine, lysine and histidine. The negatively charged (acidic) amino acids include aspartic and glutamic acid.

5.4. Nucleotide Sequencing of PBOMP Genes

Once the fragments of DNA containing the PBOMP genes have been identified, the actual nucleotide sequences of these genes can be ascertained by sequence analysis of the DNA. The sequential order of the base pairs can be determined by either of two methods, the method of Maxam and Gilbert (Maxam and Gilbert, 1980, Methods in Enzymology, 65:49) or the dideoxy method (Sanger et al., 1977, Proc. Nat'l Acad. Sci. USA 74:5463). The actual start and stop signals of the PBOMP genes can be ascertained by analysis of the nucleotide sequence for open reading frames (Rosenberg et al., 1979, Ann. Rev. Genet. 13:319). If more than one open reading frame is found on a particular DNA fragment, the identity of the actual gene could be confirmed by comparing the predicted amino acid sequence of the gene product to the amino acid sequence of the PBOMP. The location of the proper reading frame may also be determined by use of gene fusions.

5.5 Determination of Immunopotency of PBOMPs

Experience with antibodies to the capsular polysaccharide of type b *Haemophilus influenzae* i.e., PRP, shows that the ability of the antibodies to kill the bacteria in in vitro assays and to protect against challenge with Hib in animal model systems is closely correlated with the ability to elicit a protective immune response in human infants.

Anti-PBOMP antibodies elicited in response to the PBOMP proteins and peptides of this invention can be tested using similar in vitro assay systems and animal model system to demonstrate the ability to kill both Hi and Hib cells and to protect in animal model systems from challenge with Hib. The results from these systems should show a similar correlation with the potential of each of the PBOMPs to elicit a protective immune response and to serve in a vaccine for human infants, children and adults.

An in vitro complement mediated bactericidal assay system (Musher et al., 1983, Infect. Immun. 39:297-304; Anderson et al., 1972, J. Clin. Invest. 51:31-38) which has been used previously for measuring bactericidal activity of antibodies of PRP and lipopolysaccharide (LPS) against *H. influenzae* could be used to determine whether or not antibody directed against a particular PBOMP peptide or fragment thereof has bactericidal activity against type b *H. influenzae* and non-typable *H. influenzae*. These assays can be performed against a relatively large number of clinical isolates of both types of bacteria to determine whether a broad range of strains are killed. See Section 7.1 (infra) for an illustrative example of such in vitro bactericidal assay.

Further data on the ability of a PBOMP to elicit a protective antibody response may be generated by use of the infant rat meningitis model system (Smith et al., 1973, Infect. Immun. 8:278-290). Infant rats challenged before the sixth day of life, with a suitable dose of *H. influenzae* type b develop bacteremia and a fatal meningitis similar to that seen in human infants. If antibody which is bactericidal against a challenge strain is used to passively immunize infant rats prior to challenge, then they are protected from meningitis and death. Antibodies directed against the current vaccine for type b Haemophilus, PRP, are protective in the infant rat model system. Passive protection against type b Haemophilus meningitis could be demonstrated by immunizing infant rats with rabbit polyclonal anti-PBOMP antibody and subsequently challenging the rats with a lethal dose of *H. influenzae* type b. See Section 7.2 (infra) for an illustrative example of such in vivo protective antibody response elicited by the proteins and peptides of the present invention.

Data on the ability of antibody to a particular PBOMP to protect against Hi could be obtained using the chinchilla otitis media animal model system. (Barenkamp et al., 1986, Infect. Immun. 52:572–78). In this animal model, chinchillas are challenged by innoculation of the inner ear canal with Hi. An otitis media much like that seen in humans develops. Chinchillas, which have been immunized, either actively with Hi OMP's, or passively with antibody directed against Hi OMP's are protected against aural challenge with Hi. (Barenkamp et al., supra). This animal model system could be used to demonstrate the ability of antibody to a PBOMP to protect against Hi.

It is possible to demonstrate that anti-PBOMP antibodies are capable of additive protection along with anti-PRP antibodies by use of the infant rat animal model. Anti-PBOMP-1 antibodies diluted to a point at which they no longer are capable of protecting infant rats against challenge with Hib, mixed with a similar dilution of anti-PRP antibodies, may show additive protection and thus prevent death of infant rats. This additive protection might be useful for a potential combination vaccine composed of PRP, or a fragment or conjugate thereof, and the PBOMP or a fragment thereof.

5.6. Formulation of a Vaccine

Many methods may be used to introduce the vaccine formulations described below into a human or animal. These include, but are not limited to: intradermal, intramuscular, intraperitoneal, intravenous, subcutaneous and intranasal routes of administration.

5.6 1. Subunit Vaccine Formulations

One purpose of the present invention is to provide proteins or polypeptide fragments related to outer membrane proteins of *H. influenzae*, PBOMPs including PBOMP-1, PBOMP-2 and related proteins and peptides, which are used as immunogens in a subunit vaccine to protect against meningitis and other disease symptoms of *H. influenzae* infections. Subunit vaccines comprise solely the relevant immunogenic material necessary to immunize a host. Vaccines made from genetically engineered immunogens, chemically synthesized immunogens and/or immunogens comprising authentic substantially pure *H. influenzae* PBOMPs isolated as described herein, which are capable of eliciting a protective immune response are particularly advantageous because there is no risk of infection of the recipients. Thus, the PBOMP related protein or fragment thereof may be purified from recombinants that express the PBOMP epitopes. Such recombinants include any of the previously described bacterial transformants, yeast transformants, or cultured cells infected with recombinant viruses that express the PBOMP epitopes (see Sections 5.3 and 5.4., supra). Alternatively, the PBOMP related protein or peptide may be chemically synthesized. To this end, the amino acid sequence of such a protein or peptide can be deduced from the nucleotide sequence of the gene which directs its expression (see Section 5.4., supra). In yet another alternative embodiment, the PBOMP related protein or peptide is isolated in substantially pure form from cultures of *H. influenzae* (see, for example, Section 5.1., supra).

Whether the immunogen is purified from recombinants or chemically synthesized, the final product is adjusted to an appropriate concentration and formulated with any suitable vaccine adjuvant. Suitable adjuvants include, but are not limited to: surface active substances, e.g., hexadecylamine, octadecylamine, octadecyl amino acid esters, lysolecithin, dimethyl-dioctadecylammonium bromide, N, N-dicoctadecyl-N'-N-bis (2-hydroxyethyl-propane diamine), methoxyhexadecylglycerol, and pluronic polyols; plyamines, e.g., pyran, dextransulfate, poly IC, polyacrylic acid, carbopol; peptides, e.g., muramyl dipeptide, dimethylglycine, tuftsin; oil emulsions; and mineral gels, e.g., aluminum hydroxide, aluminum phosphate, etc. The immunogen may also be incorporated into liposomes, or conjugated to polysaccharides and/or other polymers for use in a vaccine formulation.

In yet another embodiment of this mode of the invention, the PBOMP related protein or peptide is a hapten, i.e., a molecule that is antigenic in that it reacts specifically or selectively with cognate antibodies, but is not immunogenic in that it cannot elicit an immune response. In such case, the hapten may be covalently bound to a carrier or immunogenic molecule; for example, a large protein such as protein serum albumin will confer immunogenicity to the hapten coupled to it. The hapten-carrier may be formulated for use as a subunit vaccine.

5.6.2. Viral Vaccine Formulations

Another purpose of the present invention is to provide either a live recombinant viral vaccine or an inactivated recombinant viral vaccine which is used to protect against meningitis and other disease symptoms of *H. influenzae*. To this end, recombinant viruses are prepared that express PBOMP related epitopes (see Sections 5.3. and 5.4., supra). Where the recombinant virus is infectious to the host to be immunized but does not cause disease, a live vaccine is preferred because multiplication in the host leads to a prolonged stimulus, therefore, conferring substantially long-lasting immunity. The infectious recombinant virus when introduced into a host can express the PBOMP related protein or polypeptide fragment from its chimeric gene and thereby elicit an immune response against *H. influenzae* antigens. In cases where such an immune response is protective against subsequent *H. influenzae* infection, the live recombinant virus itself may be used in a preventative vaccine against *H. influenzae* infection. Production of such recombinant virus may involve both in vitro (e.g., tissue culture cells) and in vivo (e.g., natural host animal) systems. For instance, conventional methods for preparation and formulation of smallpox vaccine may be adapted for the formulation of live recombinant virus vaccine expressing a PBOMP related protein or polypeptide.

Multivalent live virus vaccines can be prepared from a single or a few infectious recombinant viruses that express epitopes of organisms that cause disease in addition to the epitopes of *H. influenzae* PBOMPs. For example, a vaccinia virus can be engineered to contain coding sequences for other epitopes in addition to those of *H. influenzae* PBOMPs. Such a recombinant virus itself can be used as the immunogen in a multivalent vaccine. Alternatively, a mixture of vaccinia or other viruses, each expressing a different gene encoding for different epitopes of PBOMPs and/or other epitopes of other disease causing organisms can be formulated in a multivalent vaccine.

Whether or not the recombinant virus is infectious to the host to be immunized, an inactivated virus vaccine formulation may be prepared. Inactivated vaccines are "dead" in the sense that their infectivity has been destroyed, usually by chemical treatment (e.g., formaldehyde). Ideally, the infectivity of the virus is destroyed without affecting the proteins which carry the immunogenicity of the virus. In order to prepare inactivated vaccines, large quantities of the recombinant virus expressing the PBOMP related protein or polypeptide must be grown in culture to provide the necessary quantity of relevant antigens. A mixture of inactivated viruses which express different epitopes may be used for the formulation of "multivalent" vaccines. In certain instances, these "multivalent" inactivated vaccines may be preferable to live vaccine formulation because of potential difficulties with mutual interference of live viruses administered together. In either case, the inactivated recombinant virus or mixture of viruses should be formulated in a suitable adjuvant in order to enhance the immunological response to the antigens. Suitable adjuvants include, but are not limited to: surface active substances, e.g., hexadecylamine, octadecyl amino acid esters, octadecylamine, lysolecithin, dimethyldioctadecylammonium bromide, N, N-dicoctadecyl-N'-N-bis (2-hydroxyethyl-propane diamine), methoxyhexadecylglycerol, and pluronic polyols; plyamines, e.g., pyran, dextransulfate, poly IC, polyacrylic acid, carbopol; peptides, e.g., muramyl dipeptide, dimethylglycine, tuftsin; oil emulsions; and mineral gels, e.g., aluminum hydroxide, aluminum phosphate, etc.

5.6 3. Passive Immunity and Anti-Idiotypic Antibodies

Instead of actively immunizing with viral or subunit vaccines, it is possible to confer short-term protection to a host by the administration of pre-formed antibody against an epitope of *H. influenzae*. Thus, the vaccine formulations can be used to produce antibodies for use in passive immunotherapy. Human immunoglobulin is preferred in human medicine because a heterologous immunoglobulin may provoke an immune response to its foreign immunogenic components. Such passive immunization could be used on an emergency basis for immediate protection of unimmunized individuals exposed to special risks, e.g., young children exposed to contact with bacterial meningitis patients. Alternatively, these antibodies can be used in the production of anti-idiotypic antibody, which in turn can be used as an antigen to stimulate an immune response against *H. influenzae* PBOMP epitopes.

5.7. Diagnostic Assays

Yet another purpose of the present invention is to provide reagents for use in diagnostic assays for the detection of PBOMP antigens (and hence *H. influenzae*) in various body fluids of individuals suspected of *H. influenzae* infection.

5.7.1. Immunoassays

In one mode of this embodiment, the PBOMP related proteins and peptides of the present invention may be used as antigens in immunoassays for the detection of *H. influenzae* in various patient tissues and body fluids including, but not limited to: blood, spinal fluid, sputum, etc.

The antigens of the present invention may be used in any immunoassay system known in the art including, but not limited to: radioimmunoassays, ELISA assays, "sandwich" assays, precipitation reactions, gel diffusion precipitation reactions, immunodiffusion assays, agglutination assays, fluorescent immunoassays, protein A immunoassays and immunoelectrophoresis assays, to name but a few.

5.7.2. Nucleic Acid Hybridization Assay

In another mode of this embodiment, the novel nucleotide sequence of the genes encoding the PBOMP related protein and peptides of the present invention may be used as probes in nucleic acid hybridization assays for the detection of *H. influenzae* in various patient body fluids, including but not limited to: blood, spinal fluid, sputum, etc.

The nucleotide sequences of the present invention may be used in any nucleic acid hybridization assay system known in the art including, but not limited to: Southern blots (Southern, 1975, J. Mol. Biol. 98:508); Northern blots (Thomas et al., 1980, Proc. Nat'l Acad. Sci. USA 77:5201–05); colony blots (Grunstein et al., 1975, Proc. Nat'l Acad. Sci. USA 72:3961–65), etc.

The following series of Examples are presented for purposes of illustration and not by way of limitation on the scope of the present invention.

6. EXAMPLES: ISOLATION AND CHARACTERIZATION OF NATURAL AND RECOMBINANT DNA-DERIVED PBOMPs

6.1. Isolation, Purification and Analysis of PBOMP-1

In one series of experiments, PBOMP-1 substantially free of other cell wall components was obtained from *H. influenzae* as follows:

*H. influenzae* Eagan was grown overnight on either brain heart infusion medium containing 10 ug/ml hemin and 1 ug/ml NAD (BHI-XV) or mMIC (modification of Herriott et al., 1970, J. Bacteriol. 101: 513–16) media. Following centifugation at 10,000×g for 15 minutes at 4° C., the supernatant was discarded into Rocal II ™ disinfectant. The cell pellet was weighed and suspended in 10 mM HEPES-NaOH (pH 7.4), 1 mM EDTA, with a volume of buffer equal to about five times the wet weight of the cells. The cell suspension was then sonicated for 5 minutes in an ice bath in 100 ml aliquots with a Branson Model 350 sonifier cell disruptor (Branson Sonic Power, Danbury, Conn.) at 60% power on a pulse setting. Following sonication, the disrupted cell suspension was centrifuged at 10,000×g for 5 minutes at 4° C. to remove unbroken cells. The sedimented unbroken cells were then weighed and re-sonicated as before in a volume of 10 mM HEPES-NaOH pH 7.4, 1 mM EDTA, equivalent to about five times the wet weight of the unbroken cells. The total membrane fraction was obtained as a pellet following addition of sufficient NaCl to provide a final concentration of 0.5M NaCl and ultracentrifugation of the broken cellular material at 100,000×g for about 1 hour.

An outer membrane-cell wall complex was then obtained by removing the inner membrane components from the total membrane fraction by repeated extraction of the total membrane fraction with 1% sarcosyl, in 10 mM HEPES-NaOH, pH 7.4. The insoluble residue containing the outer membrane cell wall fraction was isolated by centrifugation at 350,000×g for 30 minutes, suspended in 50 mM Tris pH 8.0, 5 mM EDTA, and stored overnight at 4° C.

A PBOMP-1 cell wall complex was isolated from the rest of the other proteins in the outer membrane fraction by sequential extraction of the outer membrane-cell wall fraction with octylglucoside (twice), followed by sarcosyl (twice). Both detergents were used at 1% (w/v) in 50 mM Tris, 5 mM EDTA, pH 8.0. Extractions were carried out at room temperature (20° C.) for 30 minutes each. The mixture was then centrifuged at 100,000×g for 1 hour. The insoluble, sedimented material remaining after extraction with octylglucoside and sarcosyl is a PBOMP-1-cell wall complex.

Figure 1:
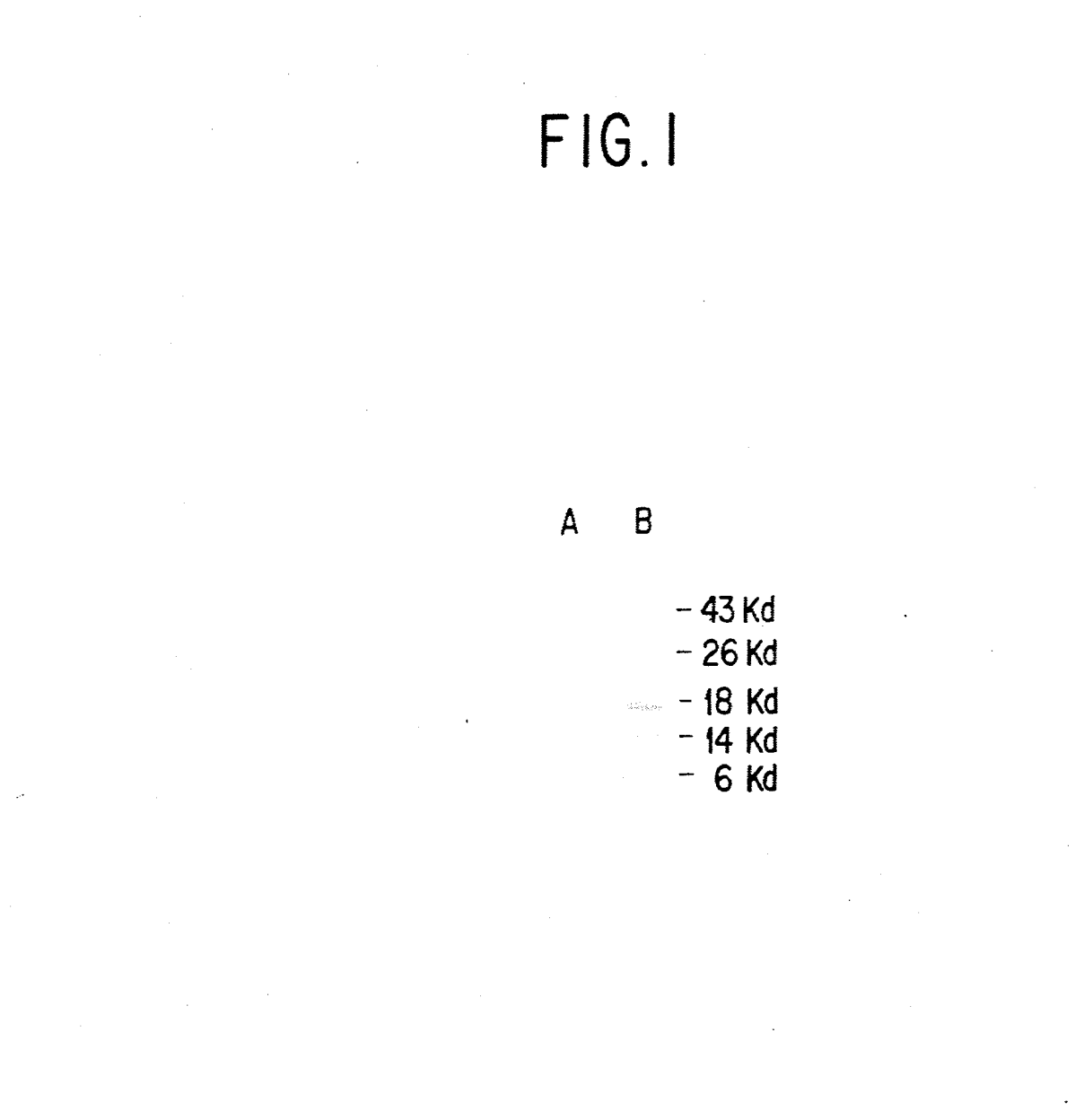

PBOMP-1 was solubilized by two methods: (1) heating to 60° C. for 1 hour in the presence of one of several detergents; or (2) disruption of the cell wall by lysozyme digestion at 37° C. for 1 hour in the presence or absence of detergent. Following either (1) or (2), soluble PBOMP-1 was separated from insoluble material by centrifugation at 100,000×g for 1 hour at 15° C. In neither procedure (1) nor (2) was the particular detergent chosen critical for the solubilization. Indeed, all detergents tested to date (including: deoxycholate, Triton X-100 TM, Tween-80, CHAPS, CHAPSO, dodecylmaltoside, zwittergent 3-14 TM and zwittergent 3-16 TM) are effective in the heat dependent solubilzation as well as the lysozyme induced solubilization. Additionally, octylglucoside is very effective in the lysozyme induced solubilizations and was used routinely at 1% (w/v) final concentration. From 40 g wet weight cells, it was possible typically to isolate about 8 mg of PBOMP-1, substantially free from other cell wall components. This substantially pure PBOMP-1 preparation was analyzed in an SDS PAGE system to determine the relative molecular weight of the reduced denatured form of this protein and to assess its purity (FIG. 1).

Samples were prepared for analysis by SDS-PAGE by adjusting them to 0.1M Tris-HCl, pH 7.0, 25 mM dithiothreitol, and 2% SDS with 5× concentrated sample buffer, then heating for 5 minutes at 100° C. Prior to electrophoresis all samples were adjusted to 6% (w/v) sucrose and 0.001% bromophenol blue. Most routine analyses were performed using the Bio-Rad Mini Protean Gel System (Redmond, Calif.) Gels were 1.5 mm thick and the separating gel contained 15% acrylamide with an acrylamide to bis ratio of 30:0.8, 0.375M Tris-HCl (pH 8.8) and 0.1% SDS. The stacking gel contained 4.8% acrylamide with the same ratio of acrylamide to bis, 125 mM Tris, HCl (pH 7.0), and 0.1% SDS per gel. Following electrophoresis gels were stained for at least 1 hour with 0.125% (w/v) Coomasie blue in ethanol: acetic acid: water (5:1:5), then destained in the same solvent system without the blue dye. Pre-stained low molecular weight standards which included the following: ovalbumin, 43,000; alpha-chymotrypsinogen, 25,700; Beta-lactoglobulin, 18,400; lysozyme, 14,300; bovine trypsin inhibitor, 6,200; insulin (A and B Chains), 2,300 and 3,400 (BRL, Bethesda, Md.) were used to assist in the determination of the relative molecular weight of the PBOMP-1.

Further purification of PBOMP-1 can be achieved by standard methods such as ion exchange chromatography, molecular sieving, hydrophobic or reserve phase chromatography, chromatofocusing, gel electrophoresis and the like.

6.1.1. Characterization of PBOMP-1 by Amino Acid Composition and Sequence

Amino acid analysis was performed according to the procedure of Simpson et al., (1976, J. Biol. Chem. 251:1936-1940). Hydrolysis was accomplished by heating 0.5-1 mg of protein in 0.1 ml 4N methane sulfonic acid under vacuum in a thick-walled sealed glass tube at 100° C. for 22 hours. The quantity of each amino acid is obtained by comparison of the areas under the various peaks with areas obtained using known quantities of standard amino acids. Results obtained are illustrated in Table 1.

TABLE 1

| AMINO ACID COMPOSITION OF PBOMP-1[a] | |
|---|---|
| Amino Acid Residues | Number |
| Aspartic Acid (Asp+Asn) | 15 |
| Threonine | 6 |
| Serine | 7 |
| Glutamic Acid (Glu+Gln) | 12 |
| Proline | 3 |
| Glycine | 18 |
| Alanine | 19 |
| Cysteine | 1 |
| Valine | 10 |
| Methionine | 0 |
| Isoleucine | 4 |
| Leucine | 11 |
| Tyrosine | 13 |
| Phenylalanine | 4 |
| Lysine | 8 |
| Histidine | 2 |
| Arginine | 7 |
| Tryptophan | 0 |

[a]The apparent molecular weight of PBOMP-1 was 15,057 daltons. The total number of amino acid residues was 140.

Initial attempts at sequencing the PBOMP-1 using Edman chemistry failed to yield satisfactory results because of a blocked N-terminal residue. In order to obtain partial amino acid sequence information, it has been necessary to enzymatically digest the 16,000 dalton molecular weight PBOMP with proteolytic enzymes to obtain peptide fragments that are amenable to sequence analysis.

A proteolytic digest of the 16,000 dalton PBOMP-1 obtained using trypsin, at 27° C. for 1 hour was separated by reverse phase high pressure liquid chromatography (RP-HPLC) using a C18 column. A large hydrophobic peptide peak (T9) was isolated and subsequently immobilized on a polybrene-coated glass fiber paper prior to the start of amino acid sequencing.

The T9 peptide was sequenced by Edman degradation (Edman et al., 1967, Eur. J. Biochem. 1:80-91). Each cycle from the sequenator generated an anilinothiazolinone phenylthiohydantoin (PTH) -amino acid. Analysis was performed on a reverse phase C18 HPLC cartridge column with a liquid chromatography system. The PTHs were eluted at room temperature with a sodium acetate-acetonitrile gradient and detected at 270 nanometers with a variable UV wavelength detector.

The sequence analysis of the T9 peptide is shown below:

Tyr-Asn-Thr-Val-Tyr-Phe-Gly-Phe-Asp-Lys-Tyr-Asp-Ile-Thr-Gly-Phe-Tyr-Val-Thr-Ile-Asp-Ala-Asp-Ala-Ala-Tyr-Leu-Asn-Ala-Thr-Pro-Ala-Ala

The T9 peptide is very hydrophobic containing 8 aromatic amino acids (5 Tyr, 3 Phe) and 5 aliphatic side chain amino acids (1 Leu, 2 Val, 2 Ile). The tyrosine content of this peptide is high but is consistent with the total amino acid composition of PBOMP-1 (Table I). Additionally, PBOMP-1 is unusual in that it contains 13 tyrosines, but no methionine or tryptophan.

6.2. Preparation of Anti-PBOMP-1 Antibodies

6.2.1. Preparation of Polyclonal Anti-PBOMP-1 Antiserum

Substantially pure PBOMP-1 was used as an immunogen to prepare anti-PBOMP-1 antibodies. Partially purified PBOMP-1 enriched fractions, prepared as described in Section 6.1, were electrophoresed on 15% SDS-PAGE gels at 35 mA constant current at 10° C. The protein bands were fixed and stained as described in Section 6.1.1. PBOMP-1 bands were excised from the gels and dialyzed against phosphate buffered saline (PBS) (20 mM sodium phosphate, 150 mM NaCl, pH 7.4) until equilibrated. The acrylamide gel fragments containing PBOMP-1 were minced by passing them through a 25 gauge needle in PBS. The fragments were injected intramuscularly into New Zealand white rabbits at multiple sites. Each rabbit received a total of approximately 20 ug of PBOMP-1. Rabbits were reimmunized at two weeks and three weeks following the initial immunization. Animals were bled one week following the last immunization and the serum collected. Animals were boosted with 20 ug of PBOMP-1 in acrylamide bimonthly to maintain high titers of anti-PBOMP-1 antibodies.

Alternatively PBOMP-1, isolated as described in section 5.1, was mixed with incomplete Freund's adjuvant and emulsified. Rabbits were injected intramuscularly with approximately 20 ug of PBOMP-1 in Freund's adjuvant. Animals were reimmunized two weeks and three weeks following the initial immunization and bled one week following the last immunization.

6.2.2. Production of Anti-PBOMP-1 Monoclonal Antibodies

Hybridoma cell lines secreting antibodies to PBOMP-1 were obtained by fusion of mouse myeloma cell line, X63.Ag8.6543 with spleen cells obtained from a C57/B1 mouse immunized against *H. influenzae* as follows: A female C57/B1 mouse was injected intraperitoneally four times over a period of two months with $1 \times 10^6$ *H. influenzae* strain S2 cells. Three months later, the mouse was immunized with substantially pure PBOMP-1 isolated from an SDS-PAGE band as described in Section 6.2.1. One month later, the mouse received an intravenous injection of total outer membranes from S2. Cell fusion was performed on the fourth day post-intravenous injection by standard procedures common to those of skill in the field (for example, Gefter et al., 1977, Somat. Cell. Genet 3:231–36).

Hybridoma cell culture supernatants were screened by a standard ELISA using *H. influenzae* outer membrane proteins as antigens. Assays were performed in 96 well polystyrene plates coated overnight at 4° C. with OMPs.

Plates were blocked with 40 mM Tris (pH 8.0), 150 mM NaCl, 5% nonfat dry milk (BLOTTO) (See Section 6.4.4) and washed with PBS/0.1% Tween-20. Culture supernatants diluted 1:10 in PBS/Tween-20 were added, incubated for 60 minutes at 25° C., and washed as before. Bound antibodies were detected with alkaline phosphatase-Goat F(ab')$_2$ anti-mouse (IgG, IgM) and the alkaline phosphatase substrate. Positive supernatants were then screened by dot blot analysis with purified PBOMP-1, *E. coli* OMP's, and S2 lipopolysaccharide (LPS). Desired hybridomas were recloned by limiting dilution (McKearn, 1980, in Monoclonal Antibodies, Kennett, McKearn and Bechtol, eds., Plenum Press, p. 374) and screened by Western blot with Hib OMP's. Selected hybridomas were injected into Balb/c mice for growth as ascites by standard procedures (Brodeur et al., 1984, J. Immunol. Meth. 71:265–72).

6.3. Reactivity of Anti-PBOMP-1 Antibodies with *E. coli*

Western blot analysis of the reactivity of anti-PBOMP-1 antiserum was performed as described in Section 6.4.4, infra. Ten microliters of an overnight bacterial culture lysed in sample preparation buffer containing 2-Mercaptoethanol was applied to each lane of a 15% SDS-PAGE gel. After electrophoresis and transfer to nitrocellulose, the blots were probed with 1:250 dilutions of rabbit polyclonal anti-PBOMP-1. Incubation with horseradish peroxidase conjugated goat anti-rabbit IgG (Kirkegaard & Perry Laboratories, Gaithersburg, Md.) showed that the anti-PBOMP-1 antisera recognized the PBOMP-1 in Haemophilus and an 18000 dalton protein in *E. coli* (FIG. 2A).

Figure 2B:
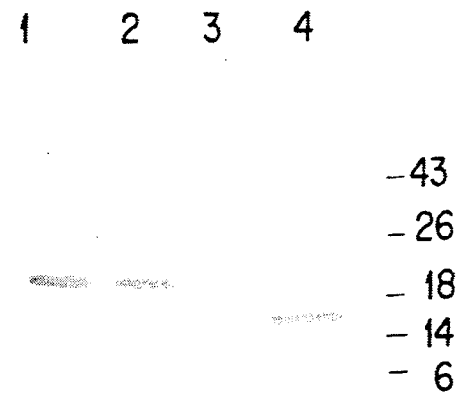

In order to confirm that an epitope of the PBOMP-1 cross-reacts with an 18000 dalton protein of *E. coli*, monoclonal antibodies made against the PBOMP-1 were screened for reactivity against *E. coli* proteins. While most of the monoclonals screened failed to react with *E. coli*, one class of monoclonals, exemplified by monoclonal G1-1, reacted strongly with the PBOMP-1 of Haemophilus and with an 18000 dalton protein in *E. coli* (FIG. 2B). This demonstrates that at least one epitope present on the PBOMP-1 cross-reacts with an epitope on an *E. coli* protein. This indicates that an antiserum against *H. influenzae* PBOMP-1 may also protect against some *E. coli* infections.

6.4. General Procedures used for Preparation of Recombinant Plasmids

6.4.1. Conditions for Restriction Enzyme Digestions

Restriction endonucleases were purchased from BRL (Bethesda, Md.), IBI (New Haven, Conn.), New England Biolabs (Beverly, Mass.), or US Biochemical Corporation (Cleveland, Ohio).

Restriction enzyme digestions were carried out by suspending DNA in the appropriate restriction buffer, adding restriction endonuclease, and incubating for an appropriate period of time to ensure complete digestion. One unit of enzyme is defined as the amount required to completely digest 1.0 ug of phage lambda DNA in 1 hour in a total reaction mixture of 20 ul volume. Buffers used with the various enzymes are listed below:

Low salt buffer used for ClaI, HpaI, HpaII, and KpnI digestions consisted of: 10 mM Tris (pH 8.0), 10 mM MgCl$_2$ and 10 mM dithiothreitol (DTT).

Medium salt buffer used for AluI, AvaI EcoRII, EcoRV, HaeII, HaeIII, HincIII, HindIII, PstI, Sau3AI, SphI, SstI, SstII, TaqI, and XhoI digestions consisted of: 50 mM Tris (pH 8.0), 10 mM MgCl$_2$, 50 mM NaCl, and 10 mM DTT.

High salt buffer used for BamHI, EcoRI, PvuI, SalI and XbaI digestions consisted of: 50 mM Tris (pH 8.0), 10 mM MgCl$_2$, 150 mM NaCl and 10 mM DTT.

The buffer used for SmaI digestions consisted of: 10 mM Tris (pH 8.0), 20 mM KCl, 10 mM MgCl$_2$, and 10 mM DTT. All restriction digestions were carried out at 37° C. except TaqI, which was carried out at 60° C.

6.4.2. Gel Purification of DNA Fragments

After restriction enzyme digestions, DNA fragments of varying sizes were separated and purified using gel electophoresis in low melting temperature agarose (FMC LGT agarose) using 50 mM Tris-acetate 1 mM EDTA buffer pH 7.8 at 10 volts/cm. Agarose concentrations varied from 0.8% to 1.5% depending on the size of fragments to be recovered. DNA bands were visualized by ethidium bromide fluorescence and cut out of the gel. DNA was recovered by melting the agarose at 65° C., adding 4 volumes of 0.65M NaCl, 10M Tris (pH 8.0), 1 mM EDTA to bring the mixture to a final concentration of 0.5M NaCl, loading the DNA onto a NACS column (BRL, Bethesda, Md.) equilibrated with 0.5 mM NaCl, 10 mM Tris pH 8.0, 1 mM EDTA (loading buffer), washing the column with 3–5 volumes of loading buffer, and eluting with 2–3 volumes 2M Nacl, 10 mM Tris pH 8.0, 1 mM EDTA. The DNA eluate was diluted 1:1 with double distilled $H_2O$ and precipitated with 3 volumes of ethanol. The pellet was washed with 70% ethanol, vacuum dried, and resuspended in 10 mM Tris-HCl buffer, pH 7.5 containing 1 mM EDTA (TE buffer).

6.4.3. DNA Ligation

All ligations were accomplished using T4 DNA ligase. T4 DNA ligase was purchased from BRL (Bethesda, Md.), United States Biochemicals (Cleveland, Ohio) or Boehringer (Indianapolis, Ind.). One unit (U) of T4 DNA ligase is defined as the amount required to yield 50% ligation of HindIII fragments of bacteriophage lambda DNA in 30 minutes at 16° C. in 20 ul volume ligase buffer at a·5'-DNA termini concentration of 0.12 uM (300 ug/ml). DNA ligations were performed in ligase buffer consisting of: 50 mM Tris (pH 7.5), 10 mM $MgCl_2$, 10 mM DTT, 1 mM adenosine triphosphate). Normally a DNA concentration ranging from 20–30 ug/ml, and a molar ratio of vector to insert of 1:1 was used. T4 DNA ligase was added at a ratio of 1 U per 20 ul reaction volume. Incubations were carried out for 18–24 hours. Temperatures used were 15° C. for cohesive end ligations, and 22° C. for blunt end ligations. If sufficient material was available, ligations were checked by analyzing a portion of the reaction mixture by agarose gel electrophoresis.

6.4.4. Protein Immuno Blot Analysis (Western Blot)

Proteins were fixed to nitrocellulose sheets for immuno blot analysis by various techniques, depending on the particular application. Phage plaques were transferred from agar plates by gently placing a sterile 8.1 cm diameter nitrocellulose disc onto the surface of a 10 cm diameter phage titer plate. The sheet was allowed to wet completely, positions were marked by punching through the filter with a sterile needle, and the filter was lifted after two minutes.

Colony blots were performed by transferring bacterial colonies to a nitrocellulose sheet, allowing the colonies to grow by placing the sheet (colony side up) on nutrient agar for 4 to 6 hours, and exposing the sheet to chloroform vapor for 30 minutes to lyse the colonies. Protein gel transfers were performed by placing an SDS-PAGE gel containing the protein mixture to be analyzed on a nitrocellulose sheet and applying horizontal electrophoresis in a Hoeffer Transphor apparatus at 0.5 A for 14 hours in 25 mM Tris 0.38M glycine pH 8.8 buffer.

Once protein transfer was complete, filters were soaked in 50 mM Tris (pH 8.0), 150 mM NaCl, 5% nonfat dry milk (BLOTTO) at 37° C. for one hour in all cases, except colony blots. When colony blots were performed, the filters were soaked overnight at 4° C. in BLOTTO containing 1 mg/ml lysozyme to digest cell debris. Filters were then absorbed with a first antibody probe at an appropriate dilution (determined by trial and error) in BLOTTO for 3 hours at 37° C., washed three times for 15 minutes with BLOTTO, absorbed with horseradish peroxidase conjugated second antibody (Kirkegaard and Perry, Gaithersburg, Md.) at a dilution of 1:500 in BLOTTO for one hour at 37° C. and washed with BLOTTO three times for 15 minutes. Filters were placed in 50 mM Tris (pH 7.0), 150 mM NaCl, 0.01% hydrogen peroxide; and 0.06% 4-Chloro-1-naphthol (Sigma Chemical Co., St. Louis, Mo.) in methanol was added. If no blue color developed within 20 minutes, the reaction was considered negative. The reaction was stopped by transferring the filter to distilled water and blotting dry.

6 4.5. Gene Fusions

Fusions of a gene or gene fragment encoding a PBOMP protein or peptide thereof to another gene such as the gene encoding alkaline phosphatase (PhoA) were carried out as described by Manoil and Beckwith (1985, Proc. Nat'l Acad. Sci. USA 82:8129–8133). Recombinant plasmids were introduced into an *E. coli* strain containing a deletion of the native PhoA gene and carrying a derivative of transposon Tn5 (TnPhoA) which contains an alkaline phosphatase gene, which lacks both a promotor and a membrane transport signal sequence, inserted into the left terminal repeat of Tn5 on an F-prime plasmid. Hence, production of active alkaline phosphatase enzyme requires transposition of TnPhoA such that the PhoA gene is fused in frame into an actively transcribed gene containing a membrane transport signal peptide. Such transpositions were detected by plating cells in the presence of 40 ug/ml 5-Bromo-4-Chloro-3-Indolyl Phosphate (XP, Sigma Chemical Co., St. Louis, Mo.). In the presence of this dye, colonies producing active alkaline phosphatase enzyme appear intensely blue in color while colonies which lack active alkaline phosphatase appear white.

6.4.6. DNA Filter Hybrdization Analysis (Southern Blot)

DNA filter hybridization analysis was carried out according to the procedure of Southern (1975, J. Mol Biol. 98: 508). DNA to be analyzed by filter hybridization was digested with appropriate restriction endonuclease(s) and separated by agarose gel electrophoresis in 0.8% Agarose (SeaKem Portland, Me.) using 90 mM Tris-borate, 8 mM EDTA buffer and 10 volts/cm. DNA in the gel was denatured by soaking the gel in 1.5M NaCl/0.5M NaOH for 1 hour and neutralized by soaking in 1.5M NaCl/1.0M Tris-HCl for 1 hour. Denatured DNA was transferred to nitrocellulose filter paper by blotting. Following transfer of DNA, filter were washed with 6×SSC (prepared by dilution from a 20×SSC stock containing 175.5 g NaCl and 88.2 g Na citrate/liter) and air dried. DNA fragments were fixed to the filter by baking at 80° C. for 2 hours under vacuum.

DNA hybridization probes were prepared by nick translation according to the procedure of Rigby et al., (1977, J. Mol. Biol., 113: 237–244). DNA for the probe (1-2 ug) was dissolved in 100 u nick-translation buffer (50 mM Tris-HCl, pH 7.4, 10 mM MgSO$_4$, 10 mM DTT, 5 ug/ml bovine serum albumin, and 20 um each dGTP, dCTP, and dTTP). To this reaction mixture, 100 uCi of alpha $^{32}$P-dATP (Amersham 2-3000 Ci/mmole), 1.0 ng of deoxyribonuclease I (Sigma Chemical Co., St. Louis, Mo.) and 10 U *E. coli* DNA polymerase I (Boehringer) were added and the mixture incubated at 15° C. for 45 minutes. The reaction was stopped by the addition of EDTA to 50 mM and heating to 65° C. for 10 minutes to inactivate the enzymes. The labeled DNA was precipitated by addition of three volumes of ethanol and resuspended to 50 ul of 0.3M ammonium acetate (NH$_4$OAc). The sample was loaded onto a 1 ml Biogel P-50 spin column equilibrated with 0.3M NH$_4$OAc and eluted by centrifugation at 500×g for 5 minutes. The column was washed with 100 ul 0.3M NH$_4$OAc and the eluates combined and precipitated with three volumes of ethanol. The labelled DNA pellet was vacuum dried, resuspended in TE buffer, radioactive incorporation measured in a Beckman (LS9000) scintillation counter by Cherenkov scattering.

For hybridization, filters with bound DNA were wetted with 6×SSC and prehybridized with 6×SSC/0.5% SDS/5X Denhardt's solution/100 ug/ml tRNA at 68° C. for 2 hours to block excess binding capacity of the filter (1×Denhardt's solution is 0.02% Ficoll., 0.02% polyvinylpyrrolidone, 0.02% bovine serum albumin in water). The hybridization reaction was carried out in the same buffer to which 0.01M EDTA and 5-10,000,000 CPM (Cherenkov) labelled probe was added. The probe solution was heated to 90° C. for 10 minutes prior to application to denature the DNA strands, cooled to 68° C., and incubated with the filter at 68° C. for 18-24 hours. After hybridization, filters were washed with several changes of 0.1×SSC/0.5% SDS at 68° C. in order to remove non-specifically bound probe. Under the conditions used, DNA homologies of greater than or equal to 90% would show positive binding of the DNA probe. Filters were air dried and exposed on Kodak XAR film at −70° C. using Dupont CRONEX 'Lightning Plus' intensifying screens.

6.5. Cloning the PBOMP Genes of *H. Influenzae*

The source of *H. influenzae* chromosomal DNA for cloning of the PBOMP genes was either *H. influenzae* KW20b (HiKW20b), a derivative of a non-encapsulated Rd stain of Hi transformed to type b+ by DNA from strain b-Eagan (Moxon et al, 1984, Clin. Invest. 73:298-306) or *H. influenzae* S2, (Hi S2), a spontaneous capsule-minus mutant of Hib Eagan.

To generate a phage lambda library, chromosomal DNA from Hi was sheared to an average length of about 15000 base pairs (bp), blunt ended by treatment with T4 DNA polymerase, modified with EcoRI DNA methylase, ligated to synthetic EcoRI linkers, and cloned into the recombinant Lambda phage vector Charon 4.

Figure 3:
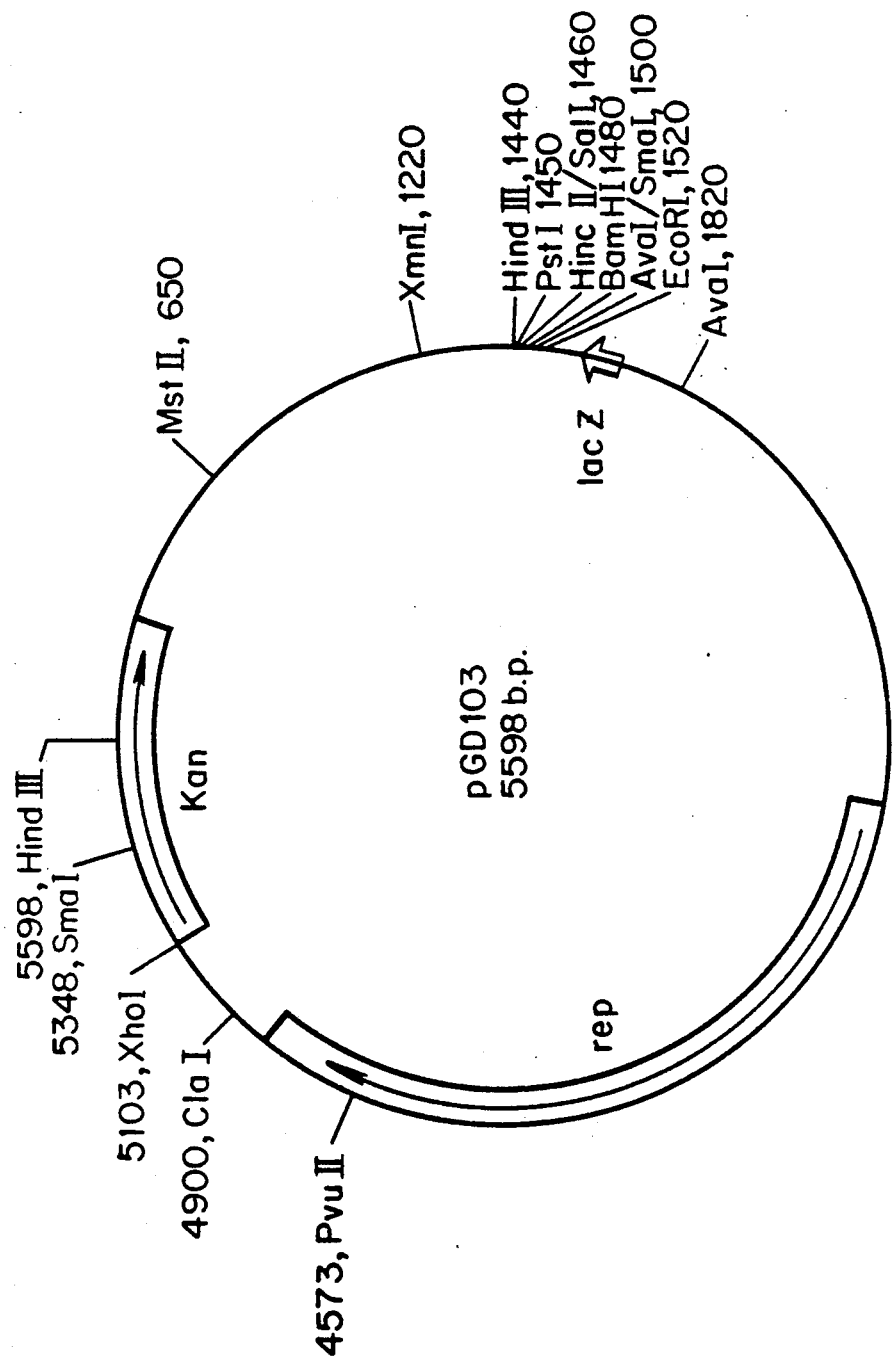

To generate a plasmid library chromosomal DNA of Hi S2 was partially cleaved with Sau3A, the 3-8 kilobase (kb) length restriction fragments thus generated were isolated, and ligated into plasmid vector pGD103 at the BamHI restriction site. This plasmid is a derivative of pLG339 (See FIG. 3; see also Stoker et al., 1982, Gene 18:335-41) and is carried in 6-8 copies/cell. It also contains the lac Z-alpha peptide and polylinker region from plasmid pUC8; and therefore, if transformed into an appropriate *E. coli* strain (such as JM83), allows selection of recombinant plasmids by screening for loss of the Lac+ phenotype. If cloned in the proper orientation, it is also possible that a cloned gene which is poorly expressed in *E. coli* could come under control of the strong, regulated lac promotor. *E. coli* containing recombinant plasmids were screened for production of PBOMPs using a pooled mixture of monoclonal antibodies or polyclonal anti-PBOMP-1 antiserum.

6.5.1 Construction of Hi Plasmid Library

It is possible that the PBOMP-1 protein is not expressed on or is incompatible with lambda phage. In order to test this we constructed a plasmid chromosomal library of Hi S2. Cloning of *E. coli* OMP genes on high copy number plasmids has been shown to be toxic (see, for example, Beck et al., 1980, Nucleic Acid Res. 8:3011-3024). In order to avoid this problem, we used the low copy number plasmid pGD103 (see FIG. 3).

Chromosomal DNA from a Hi S2 was partially digested with restriction endonuclease Sau3A (BRL, Bethesda, Md.). Five hundred micrograms of DNA was digested in 5 ml restriction buffer with 50 units of Sau3A for 1 hour at 37° C.. Fragments were separated by velocity sedimentation in a Beckman SW28 rotor on 10-40% sucrose gradients containing 10 mM Tris (pH 8.0), 1 mM EDTA, 1M NaCl at 140,000×g for 24 hours. Two ml fractions were collected and aliquots analyzed by agarose gel electrophoresis. Fractions containing restriction fragments of 3-8 Kb in length were pooled and concentrated in TE buffer. Plasmid pGD103 DNA was digested with BamHI endonuclease and treated with calf alkaline phosphatase (Boehringer, Indianapolis, Ind.) (1 Unit/ug DNA, 37° C.×30 minutes in restriction buffer). DNA was purified from the reaction mixture by phenol extraction and ethanol precipitation and resuspended in TE buffer. Since BamHI and Sau3A restriction enzymes form cohesive ends, no further treatment of DNAs prior to ligation was necessary.

About twenty-five ug each of Hi S2-Sau3A digested DNA and pGD103/BamHI/CAP digested DNA were mixed in 500 ml ligation buffer containing 25 U T4-ligase (Boehringer, Indianapolis, Ind.) and incubated at 15° C. for 18 hours. A 20 ul aliquot of the reaction mixture was analyzed by agarose gel electrophoresis in order to verify the ligation reaction (starting material was run in an adjacent lane). The ligation mixture was then transformed into competent *E. coli* JM83 (se Maniatis et al., 1982, Molecular Cloning, Cold Spring Harbor Laboratory, p. 250) incubated for 1 hour in LB-broth at 37° C., and plated on LB-agar plates containing 50 ug/ml kanamycin sulfate (Sigma Chemical Co., St. Louis, Mo.) and 40 ug/ml 5-Bromo-4-chloro-3-indolyl-Beta-D-galactopyranoside (X-gal, BRL Bethesda, Md.), and incubated 24 hours at 37° C.. About 50% of the kanamycin resistant (kanR) colonies which developed were white (Lac−), indicating insertion of S2 DNA into the BamHI site in the lac region of pGD103 (Lac+ non-recombinants are blue). Ten white colonies were selected at random, amplified, and shown to contain plasmids 4-8 Kb larger than pGD103 with insertions at the vector BamHI site.

One thousand five hundred and twenty-five white colonies were picked, amplified individually, and stored frozen at −70° C. in LB broth containing 18% sterile glycerol in 96-well microtiter dishes.

6.5.2. Construction of Hib Lambda Gene Bank

High molecular weight chromosomal DNA from Hi KW20b was suspended in TE buffer at a concentration of 200 ug/ml and sheared to an average length of 15000 bp by passage through a 25 gauge needle. Protruding ends were removed by treatment with T4 DNA polymerase in 50 mM Tris, (pH 8.8), 10 mM $MgCl_2$, 20 mM $(NH_4)_2SO_4$, 10 mM DTT, 50 uM dATP, dCTP, dGTP, and dTTP) at 37° C. for 20 minutes. DNA was then modified with EcoRI DNA methylase (1 U/ug DNA) (BRL Bethesda, Md.), in 100 mM Tris (pH 8.0), 10 mM EDTA, 0.1 mM S-adenosyl-methionine) for 3 hours at 37° C.. Methylation of DNA was verified by removing 1 ug of DNA from the reaction, mixing with 1 ug of unmodified lambda DNA and digesting in 20 ul of high salt restriction buffer with 5 units of EcoRI for 1 hour at 37° C.. Under these conditions, the modified Hi DNA was not digested, while the added lambda DNA was digested to completion.

Twenty micrograms of modified Hi DNA was ligated to 1 ug chemically synthesized EcoRI linkers (BRL Bethesda, Md.) in a 100 ul reaction mixture using T4 DNA ligase (5 U). After 18 hours, the reaction was stopped by heating to 60° C. for 20 minutes, NaCl was added to a final concentration of 150 mM, and the mixture was digested with 10 U EcoRI for 6 hours. Modified Hi DNA plus linker was separated from cleaved and unligated linkers by agarose gel electrophoresis as described above.

Prepared Hi DNA was mixed with the left and right EcoRI fragments of lambda Charon 4 DNA at a 1:1:1 molar ratio and ligated with T4 DNA polymerase for 18 hours. The ligated DNA mixture was packaged into Lambda phage particles using an in vitro packaging reaction. Five ug of ligated DNA in 4 ul $H_2O$ was added to 7 ul of 20 mM Tris (pH 8), 10 mM 2-mercaptoethanol (2-ME), 3 mM $MgCl_2$, 1 ul of 10 mM Tris, pH 7.5, 1 mM Spermidine, 2 mM putrescine, 10 mM $MgCl_2$, 1.5 mM ATP, 5 mM 2 ME and 5 ul of sonic extract from $E.$ $coli$ BHB2690 ($-$1 imm 434, $cI^{ts}$, b2.red3, Eam 15, Sam7) lysate (Hohn et al., 1977, Proc. Nat'l Acad. Sci. 74:3259). The reaction mixture was incubated at 22° C. for 1 hour and packaged phages were separated by centrifugation in a 3M to 5M CsCl [in 10 mM Tris (pH 7.5), 10 mM $MgCl_2$, 0.02% gelatin (TMG buffer)] step gradient for 250,000×g for 4 hours in a Beckman SW50.1 rotor. Phage were removed from the interface and dialyzed against TMG. Titering of the phage thus prepared indicated a library of 25-30,000 independent clones of the Hi genome had been generated. The phage library was amplified by plate amplification using $E.$ $coli$ KH802 as a phage host to yield 5 ml of phage suspension containing $10^{-9}$ plaque forming units (PFU)/ml.

6.6. Isolation of PBOMP Genes

6.6.1. Isolation of a PBOMP Gene Encoding a Protein which Reacts with Monoclonal Antibodies Against PBOMP-1

Figure 4A:
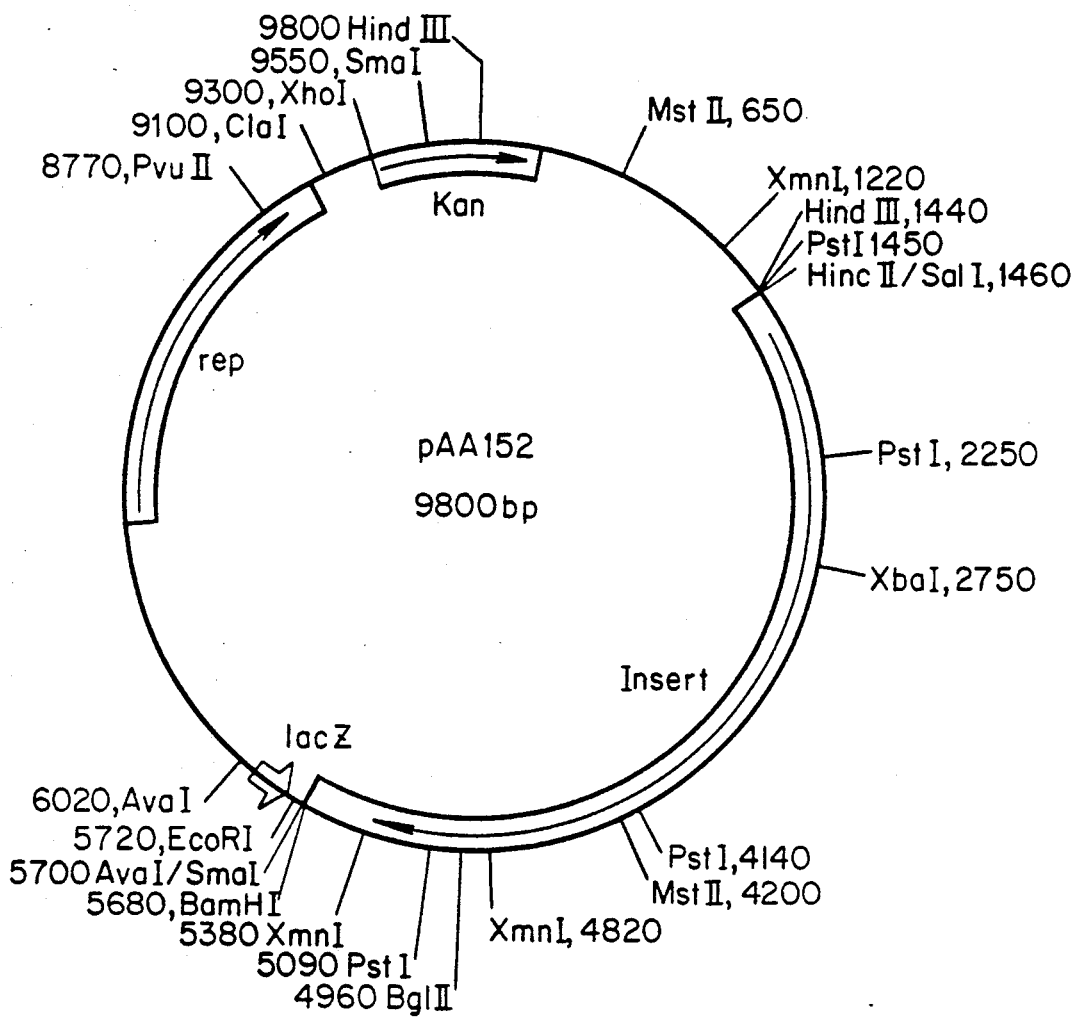
Figure 4B:
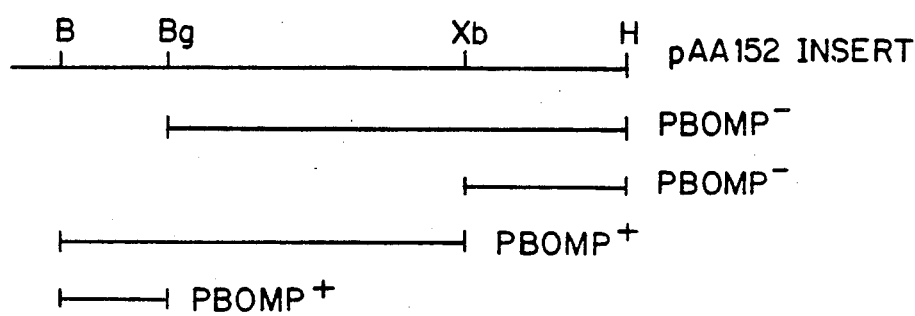
Figure 5:

The Hi plasmid library was transferred to nitrocellulose sheets on LB-kanamycin (50 ug/ml) agar, grown for 24 hours at 37° C. and analyzed by the colony blot procedure using a mixture of five non-competing monoclonal antibodies to PBOMP-1 as a probe. A clone which reacted to the mixed monoclonal probe was isolated and the plasmid designated pAA152. FIG. 4 shows a restriction map of pAA152 which contains a 4.2 Kb Hi DNA insert in vector pGD103. Western blot analysis verified that clone pAA152 expresses a 16000 dalton protein which was recognized by polyclonal anti-PBOMP-1 and also by pooled monoclonal antibody probes. Clone pAA152 was subsequently shown to produce a protein which was recognized by each individual monoclonal antibody used in the initial pool (FIG. 5).

Figure 6:
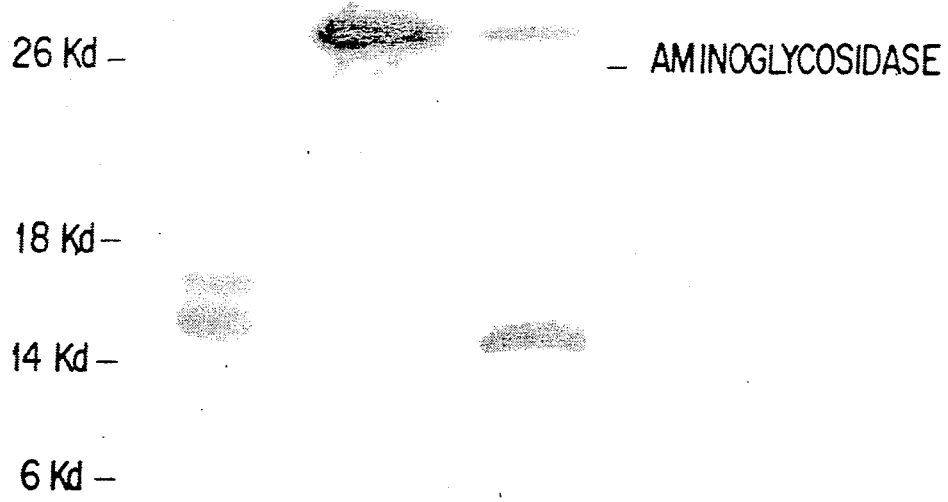

The Sau3A insert in pAA152 was found to have regenerated the BamHI site of the polylinker region at one end of the insert. Deletions from this BamHI site to either the unique BglII site or the unique XbaI site of the Hi DNA resulted in loss of expression of the PBOMP detected on Western blots. Deletions from the HincII site of the polylinker to either the XbaI or BglII sites of the Hi insert DNA retained PBOMP expression (FIG. 4). From these results, we conclude that the gene encoding this PBOMP lies in the BglII-BamHI 737 base pair fragment within the Hi DNA insert of pAA152. Analysis of minicells (Achtman et al., 1979, Proc. Nat'l Acad. Sci. USA 76:4837-41) carrying pAA152 indicated that the cloned Hi DNA encodes two proteins of 16000 and 40,000 daltons molecular weight respectively (FIG. 6). Western blots of JM83 (pAA152) show that pooled monoclonal antibodies raised against PBOMP-1 react with a 16000 dalton protein. No cross reaction is apparent within the 40,000 dalton molecular weight region.

6.6.2. Isolation of a PBOMP Gene Encoding a Protein which Reacts with Polyclonal Anti-PBOMP-1 Antisera The amplified phage library prepared as described in section 6.5.1. was diluted to 1-2000 PFU in one ml TMG and 50 ul of $E.$ $coli$ KH802 ($5 \times 10^9$ cells/ml) were added. The mixture was incubated at 37° C. for 20 minutes and plated with 3 ml soft agar on agar plates containing NZYCM medium: 10 g NZ Amine A, 5.0 g NaCl, 2.0 g $MgSO4.7H_2O$, 5 g Yeast Extract, 1 g casamino acids (per liter). Plates were incubated overnight, chilled to 4° C. for 30-60 minutes, and plaques were transferred to nitrocellulose. Filters were probed with polyclonal anti-PBOMP-1 as described above in Section 6.4.4. Several positive plaques were detected in this manner. However, no positive plaques were detected when PBOMP-1 monoclonal antibodies were used as a probe. Positive plaques were picked from the plate and amplified by growth in $E.$ $coli$ KH802. Clones were verified by SDS-PAGE gel/Western Blot analysis of phage lysates. All positive clones expressed a protein of apparent molecular weight 16000 daltons which reacted with polyclonal antibody to PBOMP-1. This protein was not present in control lysates of Charon 4 phage. In similar experiments, lysates from the positive clones failed to react with monoclonal antibodies to PBOMP-1.

One positive phage, designated lambda 16-3 was selected for further analysis. This phage isolate was amplified by growth in $E.$ $coli$ KH802 in NZYCM broth, recovered by precipitation with 20% Polyethylene glycol 6000 and banded in cesium chloride equilibrium gradients (4M CsCl in TMG, Beckman SW50.1 rotor, 300,000×g for 24 hours). Phage DNA was isolated by treatment with 0.1% SDS and 20 ug/ml proteinase K (Sigma Chemical Co., St. Louis, Mo.) at 55° C. for 1 hour followed by extraction with phenol and ethanol precipitation.

Figure 7A:
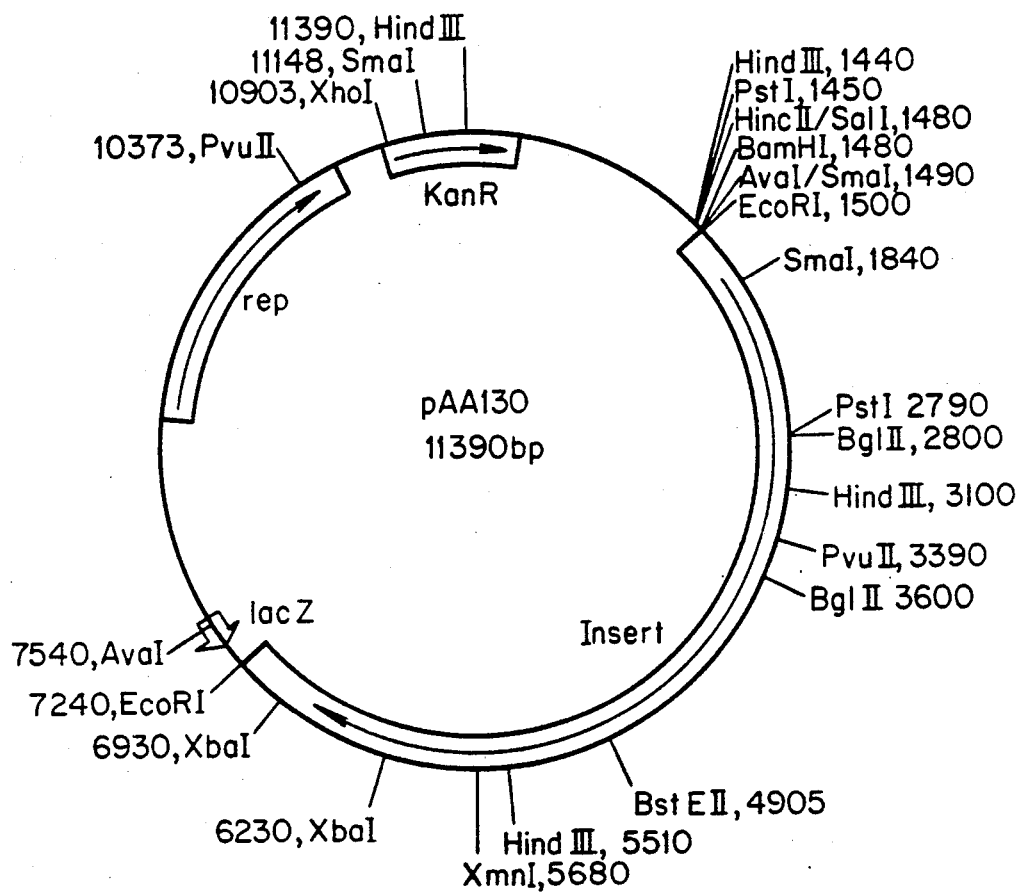
Figure 7B:
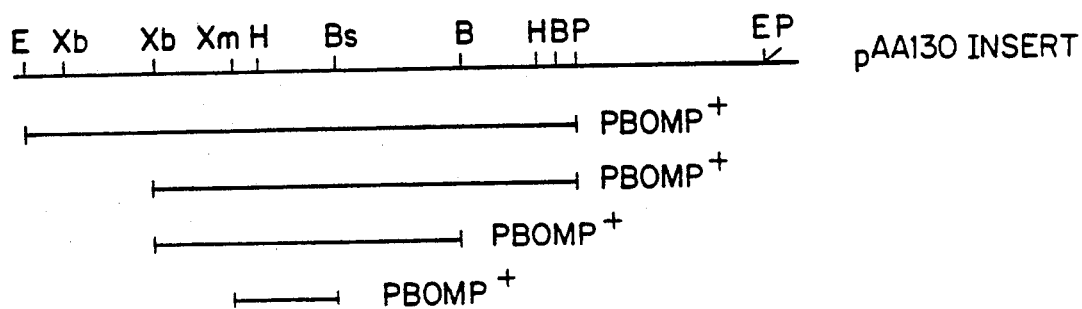

The lambda 16-3 DNA was digested with EcoRI and a partial physical map of the Hi chromosomal insert was obtained EcoRI fragments of the insert were isolated and subcloned into plasmid vector pGD103. Clones carrying fragments expressing the PBOMP-1 cross-reactive 16000 dalton protein were identified by Western blot transfer analysis of cell lysates. One of these was designated pAA130. FIG. 7 represents a restriction map of this plasmid having an 5.7 Kb fragment from Hi DNA cloned into pGD103 plasmid.

Figure 8:
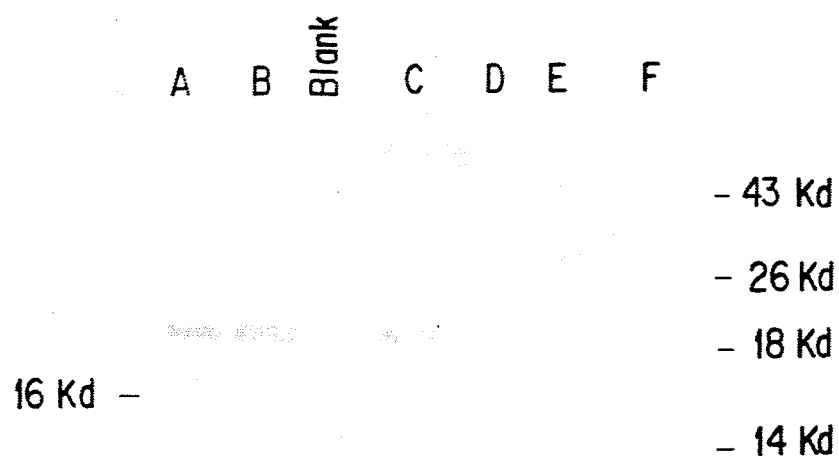
FIG. 8 represents reactivity of whole cell lysates of *E. coli* JM83 and *E. coli* JM83 containing pAA130 with polyclonal anti-PBOMP-1 antiserum. Lanes represent: (A) JM83 containing pAA130; (B) JM83 containing pAA130; (C) JM83; (D) JM83; (E) molecular weight standards as displayed in kilodaltons on the right side of the FIG.; and (F) Hi S-2.

Monoclonal antibodies against PBOMP-1 did not react with the 16000 dalton protein expressed from pAA130 (data not shown). The protein expressed by this recombinant plasmid was recognized, however, by polyclonal anti-PBOMP-1 antisera (see FIG. 8 for example).

Analysis of minicells (Achtman et al., supra) carrying pAA130 indicated that the cloned Hib DNA codes for proteins of apparent molecular weights of 16000 and 17000 daltons. The labelled 16000 dalton protein was specifically immunoprecipitated by polyclonal anti-PBOMP-1 (data not shown). Thus, plasmid pAA130 directs the expression of a 16000 dalton molecular weight PBOMP.

An internal deletion generated by excision of DNA inserted between the unique PstI site of the insert and the single PstI in the polylinker did not affect the expression of the cross-reacting protein. The XbaI fragment of this plasmid was deleted by a similar method and expression of the PBOMP-cross reacting protein was retained (FIG. 7). An additional deletion derivative of this plasmid was generated by religation of the two internal BglII sites and this derivative also retained expression of the PBOMP-cross reactive protein.

The 781 base pair BstEII-XmnI fragment was cloned by isolating the fragment from a low melting point agarose gel, filling in the BstEII end with Klenow fragment of DNA Polymerase I and cloning the fragment into the HincII site of pGD103. Western blot analysis using polyclonal anti-PBOMP-1 showed that this plasmid retained expression of the 16000 dalton PBOMP. As with pAA130, the PBOMP produced from this plasmid failed to react with monoclonal antibodies to PBOMP-1.

As an independent method of verifying the location of this PBOMP gene, the large EcoRI-PvuII fragment of pAA130 was ligated with the EcoRI-PvuII fragment of pLG339 to generate a new tetracycline resistant plasmid designated pAA136. This plasmid expressed the PBOMP as verified by Western blots. This plasmid was transformed into an E. coli strain with deletion of the chromosomal alkaline phosphatase gene (phoA) and carrying the transposible element TnPhoA. Three independent transpositions of the TnPhoA element into pAA136 which restored alkaline phosphatase activity were isolated. The sites of the TnPhoA insertions into pAA136 were determined using the unique DraI restriction site near the left terminal region of TnPhoA and the HindIII, BstEII, XmnI, and PstI sites of pAA136. All three insertions were determined to fall within the BstEII-XmnI fragment of pAA136. All three TnPho insertions were in the same orientation indicating that transcription of the PBOMP gene is directed from the BstEII site towards the XmnI site in pAA136. All three TnPhoA transpositions resulted in loss of the 16000 protein detected by polyclonal anti-PBOMP-1 antiserum as detected by Western blots. One fusion generated a new band on Western blots at 60000 dalton which was detected by polyclonal anti-PBOMP-1 antiserum. This size is within the predicted range of fusion proteins that might be generated by fusion of alkaline phosphatase (45000 daltons MW) to a 16000 dalton MW protein. Restoration of PhoA activity in these transpositions verifies that the PBOMP protein contains a peptide signal for membrane transport; and hence, is probably a membrane protein.

The TnPho fusions were sequenced by subcloning the junction between TnPhoA and the Hi cloned DNA sequences into M13. In all cases the PhoA coding sequences were determined to be in frame with the predicted open reading frame for the PBOMP-2 gene of pAA130 (see Section 6.7.2, infra).

6.7. Determination of the Nucleotide Sequence of PBOMP Genes

6.7.1. Sequencing Strategy for the PBOMP Gene Expressed by pAA152

The nucleotide sequence of the PBOMP gene expressed by pAA152 was obtained by dideoxynucleotide sequencing (Sanger et al., 1978, Proc. Nat'l Acad. Sci USA 74:5463–5467) of the 737 bp BglII-BamHI fragment of pAA152, after subcloning into single stranded phages of the M13 family, i.e., M13 mp18 and mp19.

Figure 9:
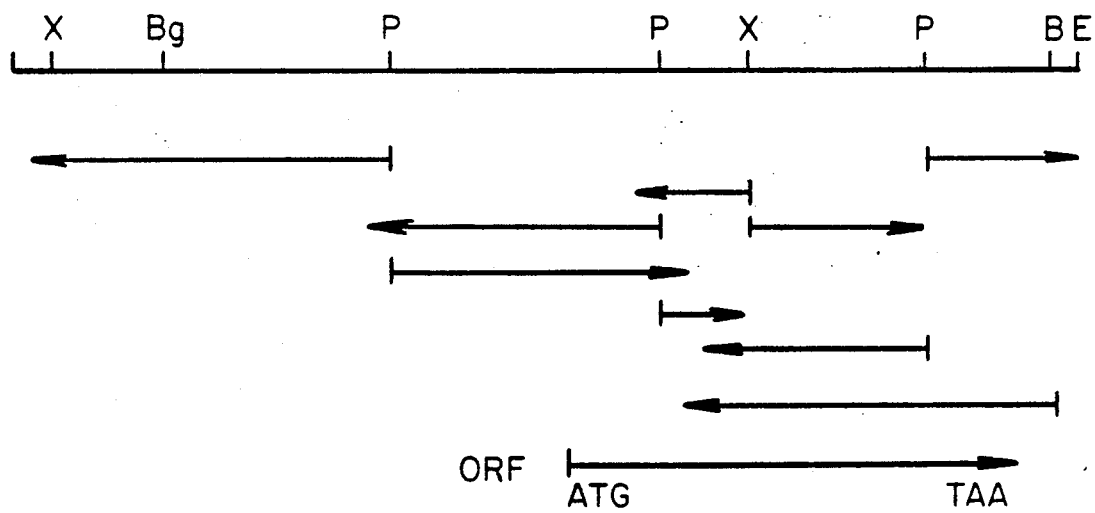
FIG. 9 represents the DNA sequencing strategy of the 737 bp insert fragment of pAA152 showing the origin, direction, and extent of sequence determined from the various clones. The arrow at the bottom denotes the location of the major open reading frame (ORF).
Figure 16:
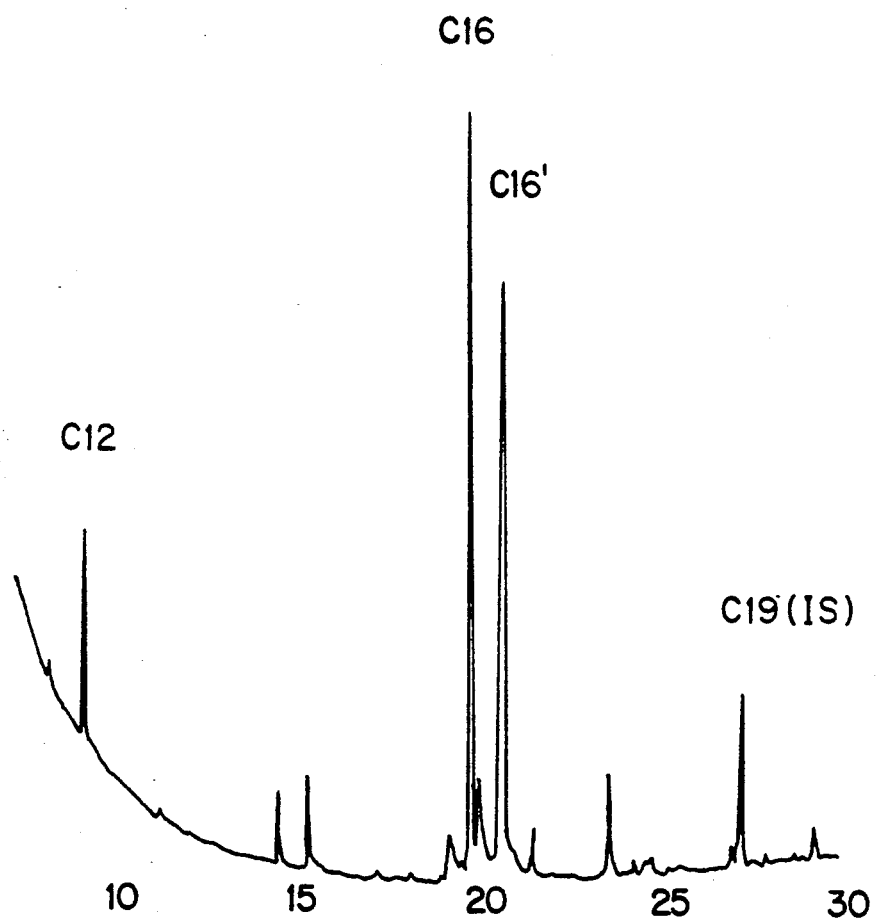

The location and direction of sequences determined from these subclones is shown in FIG. 9. The complete nucleotide sequence of the BglII-BamHI fragment is shown in FIG. 10.

The 737 BglII-BamHI fragment of pAA152 contains a single open reading frame (ORF) coding for a polypeptide of 153 amino acids (FIG. 11). The amino acid composition of the PBOMP gene determined from the DNA sequence closely matches the amino acid composition of the PBOMP-1 purified protein (see Tables 1 and 2).

TABLE 2

| DEDUCED AMINO ACID COMPOSITIONS OF MATURE PBOMP-1 AND PBOMP-2 | | |
|---|---|---|
| Amino Acid Residues | Mature PBOMP-1 of pAA152[a] | Mature PBOMP-2 of pAA130[b] |
| Aspartic Acid | 9 | 6 |
| Asparagine | 8 | 4 |
| Threonine | 7 | 5 |
| Serine | 6 | 13 |
| Glutamic Acid | 7 | 5 |
| Glutamine | 5 | 7 |
| Proline | 3 | 1 |
| Glycine | 16 | 24 |
| Alanine | 21 | 16 |
| Cysteine | 1 | 1 |
| Valine | 10 | 18 |
| Methionine | 0 | 1 |
| Isoleucine | 3 | 13 |
| Leucine | 9 | 5 |
| Tyrosine | 11 | 2 |
| Phenylalanine | 3 | 2 |
| Lysine | 7 | 7 |
| Histidine | 2 | 0 |
| Arginine | 6 | 6 |
| Tryptophan | 0 | 0 |

[a]The apparent molecular weight of mature PBOMP-1 was 14,238 daltons. The number of amino acid residues was 134.
[b]The apparent molecular weight of mature PBOMP-2 was 13,461. The number of amino acid residues was 136.

In addition, the PBOMP-1 gene has an internal peptide sequence (AA 48-81) in which (30/33) amino acids align with the amino acid sequence of the T9 internal peptide of PBOMP-1 if an allowance is made for the Leu-68 residue which is absent from the sequence of the T9 peptide (FIG. 12). The amino terminal region of PBOMP-1 also contains an amino acid sequence which shows similarities with other membrane transport peptide sequences (Watson, 1984, Nucleic Acids Res. 12:5145-5164). From these data and from the monoclonal antibody binding data, we conclude that this gene encodes the PBOMP-1 protein.

6.7.2. Sequencing Strategy for the PBOMP Gene of pAA130

The nucleotide sequence of the PBOMP gene of pAA130 was determined by dideoxynucleotide sequencing (Sanger, et al., supra) of the 789 base pair BstEII-XmnI fragment of pAA130 after subcloning into M13 mp18 and mp19 phage. These recombinant phage are designated M18001 and M19001 respectively. The universal 17 base oligonucleotide sequencing primer (New England Biolabs) was used to determine the sequence from both ends of the BstEII-XmnI fragment (see FIG. 13). Two additional oligonucleotides were synthesized and used as primers for dideoxynucleotide sequencing (M18PRI, M19PR2). All other sequencing primers were made at Praxis Biologics, Rochester, N.Y. on an Applied Biosystems 380 B DNA synthesizer. The primers were made on a 1 umole controlled pore glass column with beta-cyanoethyl phosphate protecting group chemistry. The yield of oligonucleotide was sufficiently pure to allow the use of the primers directly from the column without further purification. The two synthetic oligonucleotide primers bind to sequences approximately 200 nucleotides in from each end of the fragment as shown in FIG. 13. The total 789 bp DNA sequence of the BstEII-XmnI fragment of pAA130 is shown in FIG. 14. The ORF is underlined as shown in FIG. 15. Thus ORF encodes a polypeptide of 154 amino acids. The amino terminal 18 residue peptide resembles a membrane transport signal sequence determined for other proteins (Watson, 1984, supra). In addition, sequence data from the TnPhoA fusions in pAA130 demonstrated that all three transpositions were into the reading frame of the 154 amino acid polypeptide.

The amino acid composition of the proposed mature gene product as deduced from the DNA sequence of the ORF of pAA130 differs significantly from that determined by amino acid analysis of purified PBOMP-1 (Tables 1 and 2). No significant homology was found when the amino acid sequence of the PBOMP gene of pAA130 was compared to that of the tryptic peptide T9 from purified PBOMP-1 protein. In addition, although the product encoded by this gene is recognized by polyclonal anti-PBOMP-1 antisera, it is not recognized by monoclonal antibodies to PBOMP-1. From these observations, it is clear that the Hi gene expressed by pAA130 is not the gene for PBOMP-1. Thus the PBOMP-gene encoded by pAA130 was designated PBOMP-2.

7. EFFICACY OF PBOMP-1 SUBUNIT VACCINES

7.1. Bactericidal Activity of Anti-Sera Induced by PBOMP-1

Anti-PBOMP-1 polyclonal rabbit antisera, prepared as described in Section 6.2., were examined for their ability to kill Hib and Hi in an in vitro complement mediated bactericidal assay system (see Musher et al., 1983, Infect. Immun. 39:297-304; Anderson et al., 1972, J. Clin. Invest. 51:31-38). Sources of complement used for the assay system were either pre-collostral calf serum (PCCS) or normal rabbit serum (NRS) which had been absorbed previously with a non-typable Hi strain, S2, to remove any pre-existing anti-Haemophilus antibodies. The PCCS was used undiluted and the NRS was used at a dilution of 1:4 for Hib and 1:8 for non-typable Hi. All dilutions were prepared using phosphate-buffered saline [20 mM phosphate buffer (pH 7.4), 0.15M NaCl containing 0.15 mM $MgCl_2$ and 0.5 mM $CaCl_2$ (PCM)]. Bacterial strains to be tested were grown in BHI-XV until they reached a concentration of $1 \times 10^9$ cells/ml as measured by optical density at 490 mm. Bacteria were diluted to a final concentration of 1250 cells/20 ul in PCM. Twenty microliters of an appropriate antibody dilution in PCM was mixed with 20 ul of complement source on ice in wells of a 24 well microtiter plate (Costar). The microtiter plate was removed from ice and 20 ul of test diluted bacteria were added to each well. Wells containing no antibody served as negative controls. After 30 minutes incubation at 37° C., 800 ul of BHI-XV, containing 0.75% agarat 56° C., were added to each well and allowed to solidify at room temperature. The plates were incubated overnight at 37° C. and read the next day.

The BC titer of an antisera was read as the reciprocal of the highest dilution capable of killing 50% of the test bacteria as compared to non-antibody control wells.

The anti-PBOMP-1 was tested for bactericidal (BC) activity against several Hib clinical and laboratory isolates and the results shown in Table 3.

TABLE 3

BC ACTIVITY OF ANTI-PBOMP-1 ANTISERA AGAINST LABORATORY & CLINICAL STRAINS OF *HAEMOPHILUS INFLUENZAE*

| LABORATORY STRAINS | KILLED BY ANTI-PBOMP-1 |
|---|---|
| H. influenzae type a HST-1 | +[a/] |
| H. influenzae type c HST-5 | +/−[b/] |
| H. influenzae type b HST-3 | + |
| H. influenzae type b HST-10 | + |
| H. influenzae type b HST-12 | + |
| N.T. H. influenzae S-2 | ± |
| N.T. CLINICAL STRAINS | |
| N.T. H. influenzae HST-31 | + |
| N.T. H. influenzae HST-35 | + |
| HIB CLINICAL STRAINS | |
| 112 strains tested | 112 strains killed |

[a]+ = 50% killing of test bacteria
[b]+/− = approximately 50% of test bacteria survived As can be seen from Table 3, anti-PBOMP-1 antibody had BC activity against a wide variety of clinical insolates both typable (e.g. a, b, c) and non-typable *H. influenzae* strains. One hundred and twelve out of 112 Hib clinical isolates were killed by anti-PBOMP-1 antisera. These strains were isolated in the Southwestern U.S., the Northeastern U.S. and Western Canada.

In order to eliminate the possibility that the killing was the result of anti-LPS antibody, the BC assay was performed with 200 ng of LPS from the Hib strain used to prepare the immunogen in each well. Results of these experiments are shown in Table 4.

TABLE 4

BACTERICIDAL ACTIVITY OF ANTISERA ABSORBED WITH LPS

| ANTISERUM | LPS[a] | TEST BACTERIA | TITER[b] |
|---|---|---|---|
| PBOMP-1 | + | N.T. H. influenzae | 40 |
| | − | N.T. H. influenzae | 160 |
| | + | Hib Eagan | 40 |
| | − | Hib Eagan | 40 |
| PRP-CRM | + | N.T. H. influenzae | 10 |
| | − | N.T. H. influenzae | 10 |
| | + | Hib Eagan | 400 |

TABLE 4-continued

BACTERICIDAL ACTIVITY OF ANTISERA ABSORBED
WITH LPS

| ANTISERUM | LPS[a] | TEST BACTERIA | TITER[b] |
|---|---|---|---|
| | — | Hib Eagan | 800 |

[a]ZERO or 200 ng Hib Eagan LPS used per well
[b]Expressed as reciprocal of highest dilution of antisera showing 50% bacterial survival The LPS lowered the titer of the anti-PRP two-fold, the titer of the anti-PBOMP-1 against Hi four-fold and the titer of anti-PBOMP-1 against Hib not at all. While the LPS is reduced the BC activity of anti-PBOMP-1, it did not eliminate it. Some of the observed reduction was undoubtably the result of anti-complementary activity of the LPS, as demonstrated by the reduction of the anti-PRP BC titer.

7.2. Infant Rat Protection from *H. Influenzae*

Infant rat protection studies were performed according to Smith et. al. (1973, Pediatrics 52:637–644). Sprague-Dawley infant rats were passively immunized with 0.1 ml of varying dilutions of rabbit antisera in PCM by intraperitoneal inoculation on day four of life. Eighteen hours post-immunization, the rats were challenged intraperitoneally with $10^4$–$10^6$ Hib cells in 0.1 ml of PCM. Survival of challenged rats at 72 hours post-infection indicated protection. Results of these experiments are shown in Table 5.

TABLE 5

INFANT RAT PROTECTION BY ANTI-PBOMP-1

| Hib Challenge Strain | Antiserum Passively Transferred | Antiserum Dilution | Challenge Dose | Survivors/Total |
|---|---|---|---|---|
| HST-60 | NRS | 1/10 | $10^6$ | 0/6 |
| | PBOMP-1 | 1/10 | $10^6$ | 5/5 |
| | PBOMP-1 | 1/30 | $10^6$ | 6/6 |
| | PBOMP-1 | 1/90 | $10^6$ | 6/6 |
| HST-61 | NRS | 1/10 | $10^5$ | 0/5 |
| | PBOMP-1 | 1/10 | $10^5$ | 6/6 |
| | PBOMP-1 | 1/30 | $10^5$ | 6/6 |
| | PBOMP-1 | 1/90 | $10^5$ | 3/5 |
| Eagan | NRS | 1/10 | $10^4$ | 0/4 |
| | PBOMP-1 | 1/10 | $10^4$ | 3/5 |
| | PBOMP-1 | 1/30 | $10^4$ | 5/5 |
| | PBOMP-1 | 1/90 | $10^4$ | 0/5 |

The results in Table 5 indicate that infant rats are protected against challenge with a fatal dose of Hib by passively transferred anti-PBOMP-1 antibody. The additional clinical Hib strains which were used as challenge strains in the infant rat meningitis model to demonstrate protection that anti-PBOMP-1 protects against heterologous Hib clinical isolates.

To determine whether anti-PBOMP-1 blocks the protective effects of anti-PRP or has additive effects, infant rats were passively immunized with anti-PRP and anti-PBOMP-1 diluted beyond their protective end points. Upon challenge with Hib, the antisera together were able to protect high dilutions than either one above (Table 6). These results shown in Table 6 indicate that anti-PBOMP-1 antibody and anti-PRP antibody do not interfere with each other and are capable of giving additive protection the infant rat meningitis model.

TABLE 6

ANTI-PBOMP-1 + ANTI-PRP INFANT STUDIES
SERA INJECTED

| ANTI-PBOMP-1 (1:100)[a] | anti-PRP[b] | SURVIVORS/TOTAL[c] |
|---|---|---|
| — | — | 0/6 |
| + | — | 1/6 |
| — | 1:2000 | 2/6 |
| + | 1:1000 | 6/6 |
| + | 1:3000 | 5/6 |
| + | 1:4000 | 4/6 |

[a]Polyclonal rabbit anti PBOMP-1 diluted in PCM.
[b]Polyclonal rabbit anti-PRP:CRM$_{197}$ conjugate.
[c]Infant Sprague-Dawley rats surviving at 72 hours post-challenge.

8. DEPOSIT OF MICROORGANISMS

The following *E. coli* strains carrying the listed plasmids have been deposited with the Agricultural Research Culture Collection (NNRL), Peoria, Ill. and have been assigned the following accession numbers:

| *E. Coli* Strain | Plasmid | Accession Number |
|---|---|---|
| JM 83 | pAA152 | B18155 |
| JM 83 | pAA130 | B18154 |
| JM 83 | pGD103 | B18153 |

The present invention is not to be limited in scope by the microorganisms deposited since the deposited embodiment is intended as a single illustration of one aspect of the invention and the many microorganisms which are functionally equivalent are within the scope of the present invention. Indeed, various modifications of the invention in addition to those shown and described herein will become apparent to those skilled in the art from the foregoing description and accompanying figures. Such modifications are intended to fall within the scope of the appended claims.

It is also to be understood that all base pair sizes given for nucleotides are approximate and are used for purposes of description.

What is claimed is:

1. A subunit vaccine formulation, comprising an immunologically effective amount of a substantially pure peptide or protein having an epitope of PBOMP-1 which is an outer membrane protein of *Haemophilus influenzae* of approximately 16000 daltons molecular weight having an amino acid sequence substantially as depicted in FIG. 11 from amino acid residue 20 to 153, in which the peptide or protein is obtained without the use of denaturing detergents, and a physiologically acceptable carrier, said vaccine formulation effective against both typable and non-typable *H. influenzae*.

2. A subunit vaccine formulation, comprising an immunologically effective amount of a substantially pure peptide or protein having an epitope of PBOMP-2 which is an outer membrane protein of *Haemophilus influenzae* of approximately 16000 daltons molecular weight having an amino acid sequence substantially as depicted in FIG. 15 from amino acid residue 19 to 154, and a physiologically acceptable carrier, said vaccine formulation effective against both typable and non-typable *H. influenzae*.

3. The subunit vaccine formulation according to claim 1, in which the peptide or protein was purified from a cultured cell containing a nucleotide sequence that regulates gene expression so that the peptide or protein is expressed by the cultured cell.

4. The subunit vaccine formulation according to claim 2, in which the peptide or protein was purified from a cultured cell containing a nucleotide sequence that regulates gene expression so that the peptide or protein is expressed by the cultured cell.

5. The subunit vaccine formulation according to claim 3, in which the cultured cell is a microorganism.

6. The subunit vaccine formulation according to claim 4, in which the cultured cell is a microorganism.

7. The subunit vaccine formulation according to claim 3, in which the cultured cell is a bacterium.

8. The subunit vaccine formulation according to claim 4, in which the cultured cell is a bacterium.

9. The subunit vaccine formulation according to claim 3, in which the cultured cell is a yeast.

10. The subunit vaccine formulation according to claim 4, in which the cultured cell is a yeast.

11. The subunit vaccine formulation according to claim 3, in which the cultured cell is an animal cell line.

12. The subunit vaccine formulation according to claim 4, in which the cultured cell is an animal cell line.

13. The subunit vaccine formulation according to claim 3, in which the cultured cell is an insect cell line.

14. The subunit vaccine formulation according to claim 4, in which the cultured cell is an insect cell line.

* * * * *